US012577574B2

(12) United States Patent
Green et al.

(10) Patent No.: US 12,577,574 B2
(45) Date of Patent: Mar. 17, 2026

(54) ULTRASPECIFIC RIBOREGULATORS HAVING ROBUST SINGLE-NUCLEOTIDE SPECIFICITY AND IN VITRO AND IN VIVO USES THEREOF

(71) Applicant: ARIZONA BOARD OF REGENTS ON BEHALF OF ARIZONA STATE UNIVERSITY, Scottsdale, AZ (US)

(72) Inventors: Alexander Green, Scottsdale, AZ (US); Fan Hong, Mesa, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 350 days.

(21) Appl. No.: 18/311,587

(22) Filed: May 3, 2023

(65) Prior Publication Data

US 2024/0043853 A1 Feb. 8, 2024

Related U.S. Application Data

(62) Division of application No. 16/322,719, filed as application No. PCT/US2017/044810 on Aug. 1, 2017, now Pat. No. 11,680,269.

(60) Provisional application No. 62/369,298, filed on Aug. 1, 2016.

(51) Int. Cl.
| | |
|---|---|
| *C12N 15/67* | (2006.01) |
| *C12Q 1/6825* | (2018.01) |
| *C12Q 1/6897* | (2018.01) |

(52) U.S. Cl.
CPC ........... *C12N 15/67* (2013.01); *C12Q 1/6825* (2013.01); *C12Q 1/6897* (2013.01)

(58) Field of Classification Search
None
See application file for complete search history.

(56) References Cited

U.S. PATENT DOCUMENTS

| | | | |
|---|---|---|---|
| 10,550,440 | B2 | 2/2020 | Green et al. |
| 2015/0275203 | A1 | 10/2015 | Green et al. |
| 2019/0185856 | A1 | 6/2019 | Green et al. |
| 2019/0218624 | A1 | 7/2019 | Green et al. |
| 2019/0256898 | A1 | 8/2019 | Green et al. |
| 2019/0276901 | A1 | 9/2019 | Green |
| 2019/0285620 | A1 | 9/2019 | Green et al. |
| 2019/0382746 | A1 | 12/2019 | Green |
| 2020/0071777 | A1 | 3/2020 | Green et al. |
| 2020/0080137 | A1 | 3/2020 | Green et al. |
| 2020/0386750 | A1 | 12/2020 | Green et al. |
| 2021/0108257 | A1 | 4/2021 | Green |
| 2021/0292772 | A1 | 9/2021 | Green et al. |

FOREIGN PATENT DOCUMENTS

| | | | | |
|---|---|---|---|---|
| WO | 2004046321 | A1 | 6/2004 | |
| WO | WO-2014074648 | A2 * | 5/2014 | ............ C12N 15/67 |
| WO | 2017087530 | A1 | 5/2017 | |
| WO | 2017147585 | A1 | 8/2017 | |
| WO | 2020220013 | A1 | 10/2020 | |

OTHER PUBLICATIONS

Butler, T. M., et al. "Exome Sequencing of Cell-Free DNA from Metastatic Cancer Patients Identifies Clinically Actionable Mutations Distinct from Primary Disease," PLoS ONE 10, e0136407 (2015).

Elshimali, Y. I., et al. "The Clinical Utilization of Circulating Cell Free DNA (CCFDNA) in Blood of Cancer Patients," International Journal of Molecular Sciences 14, 18925-18958 (2013).

Green, A.A., et al. Toehold switches: de-novo-designed regulators of gene expression. Cell 159, 925-939 (2014).

International Search Report and Written Opinion for International Patent Application No. PCT/US2017/044810 with a date of mailing of Oct. 20, 2017.

Kierzek, E. et al. The thermodynamic stability of RNA duplexes and hairpins containing N6-alkyladenosines and 2-methylthio-N6-alkyladenosines. Nucleic acids research 31, 4472-4480 (2003).

Krishnamurthy et al. Tunable Riboregulator Switches for Post-transcriptional Control of Gene Expression. 2015 ACS Synthetic Biology 4(12), p. A-I (Year: 2015).

Mathews, D.H., et al. Expanded sequence dependence of thermodynamic parameters improves prediction of RNA secondary structure. Journal of molecular biology 288, 911-940 (1999).

Miller M. D., "K65R, TAMs and tenofovir," AIDS reviews 6, 22-33 (2004).

Pardee, K. et al. Paper-based synthetic gene networks. Cell 159, 940-954 (2014).

Pardee, K. et al, Rapid, Low-Cost Detection of Zika Virus Using Programmable Biomolecular Components, Cell. May 19, 2016, vol. 165, No. 5, pp. 1255-1266; p. 1260, 2nd col. 2nd paragraph; DOI: 10.1016/j.cell.2016.04.059.

Regmi S. M., et al. "Polymorphisms in drug-resistant-related genes shared among drug-resistant and pan-susceptible strains of sequence type 10, Beijing family of Mycobacterium tuberculosis," International Journal of Mycobacteriology 4, 67-72 (2015).

Straimer, J., et al., "K13-propeller mutations confer artemisinin resistance in Plasmodium falciparum clinical isolates," Science 347, 428-431 (2015).

Wang, J., et al, "Subtyping Clinical Specimens of Influenza A Virus by Use of a Simple Method to Amplify RNA Targets," Journal of Clinical Microbiology 51, 3324-3330 (2013).

(Continued)

*Primary Examiner* — Jennifer Dunston
*Assistant Examiner* — Tiffany Nicole Grooms
(74) *Attorney, Agent, or Firm* — Quarles & Brady, LLP

(57) ABSTRACT

Provided herein are highly sensitive compositions and methods for detection of at least one specific nucleic acid molecule in a sample. The presence of a specific nucleic acid provides a positive indicator of a pathogenic agent, contaminant, non-canonical bases, and/or wild-type or mutated genes in a sample or a cell. Applications for which the compositions and methods are particularly well suited include point-of-care disease diagnosis or cellular RNA imaging.

20 Claims, 20 Drawing Sheets

Specification includes a Sequence Listing.

(56)                    References Cited

OTHER PUBLICATIONS

Wang, W. et al, "PCR for Detection of Oseltamivir Resistance
Mutation in Influenza A(H7N9) Virus," Emerging Infectious Dis-
eases 20, 847-849 (2014).
Yamaguchi, T. et al, "Evolution and Single-Nucleotide Polymorphisms
in Methicillin-Resistant *Staphylococcus aureus* Strains with Reduced
Susceptibility to Vancomycin and Daptomycin, Based on Determi-
nation of the Complete Genome," Antimicrobial Agents and Che-
motherapy 59, 3585-3587 (2015).
Zong, C., et al. Genome-wide detection of single-nucleotide and
copy-number variations of a single human cell. Science 338,
1622-1626 (2012).

* cited by examiner

FIGS. 1A-1C, CONTINUED
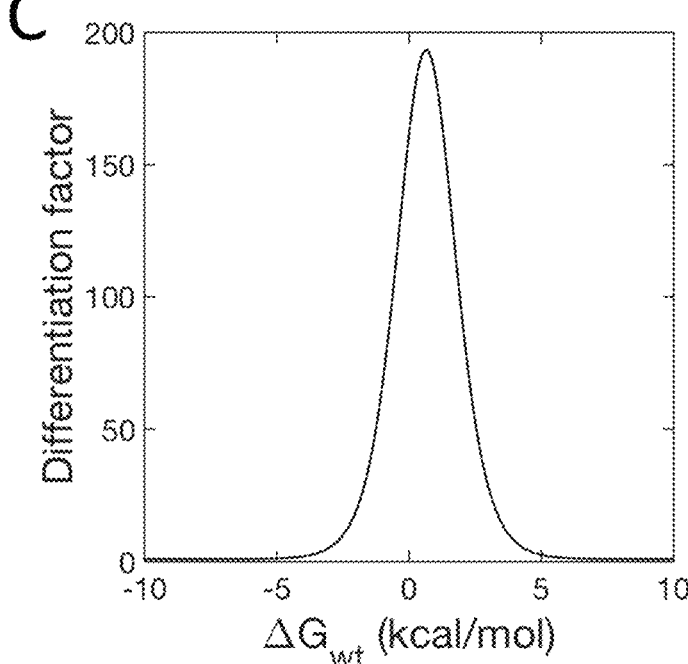
B $\quad OFFstate \rightleftharpoons ONstate$
$$\theta_{on} = \frac{1}{e^{\frac{\Delta G}{RT}} + 1}$$
$$Df = \frac{\theta_{mut}}{\theta_{wt}} = \frac{e^{\frac{\Delta G_{wt}}{RT}} + 1}{e^{\frac{\Delta G_{mut}}{RT}} + 1}$$
C

FIGS. 6A-6E, CONTINUED
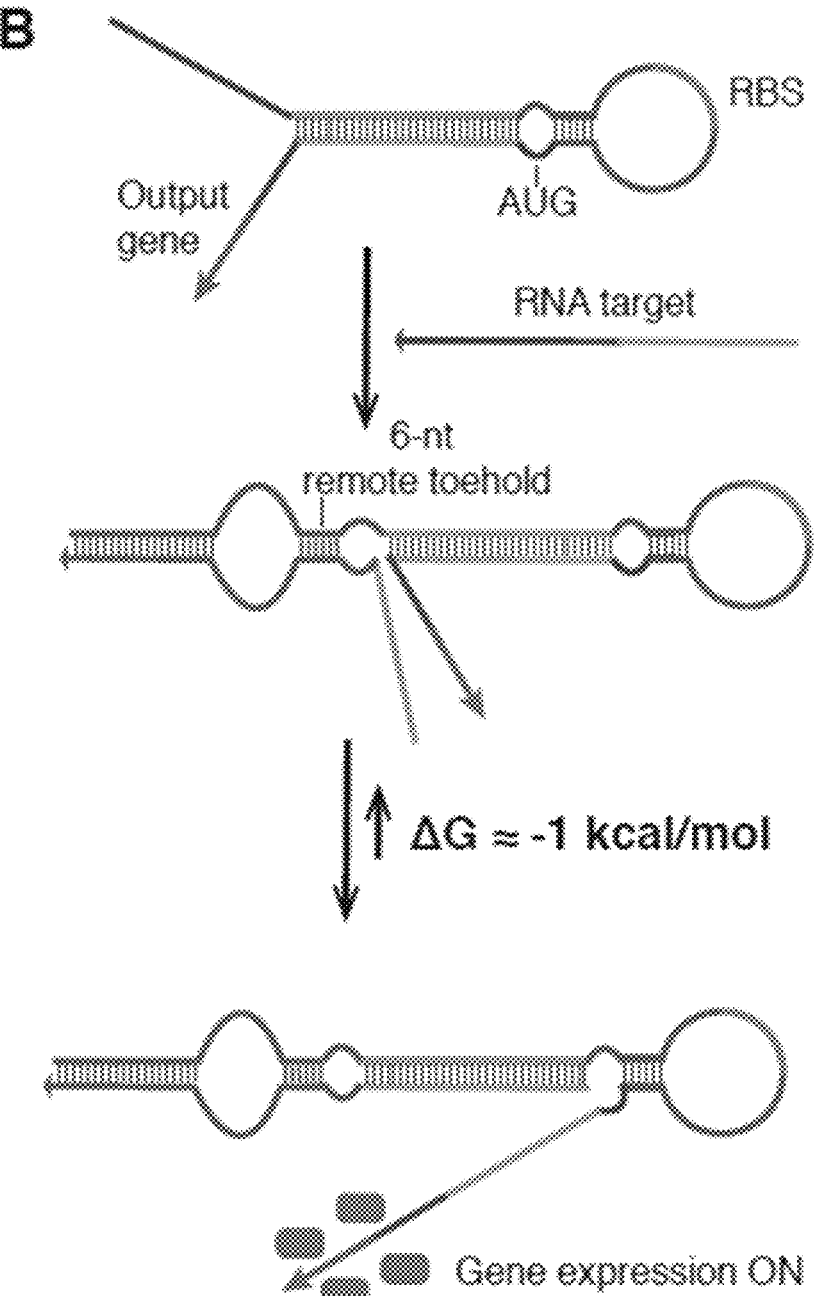

FIGS. 6A-6E, CONTINUED
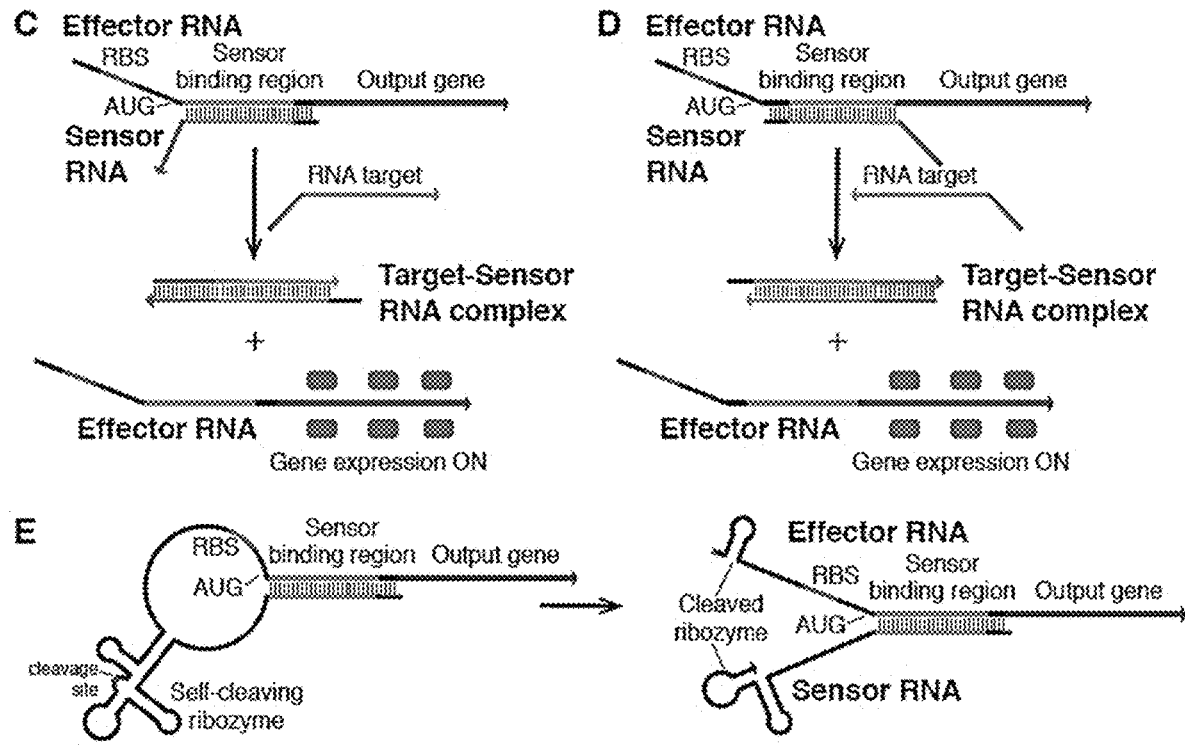

A

HIV WT:5'-...UAUCAAUACAUGGAUGAUU...-3' (SEQ ID NO:122)
HIV MUT: 5'-...UAUCAAUAUAUGGAUGAUU...-3' (SEQ ID NO:123)

HIV WT:5'—...UAUCAAUACAUGGAUGAUUUGUAUGUAG...–3' (SEQ ID NO:124)

A America Strain 5'..GUGAGGAACGGCAAUGAGAUCGCAGCUUGUCUGA..3'
(SEQ ID NO:125)

Asian Strain 5'..GUGAGGAAUGGCAAUGAGAUCGCAGCUUGUCUGA..3'
(SEQ ID NO:126)

Africa Strain 5'..GUGAGAAACGGAAAUGAAAUCGCAGCCUGUCUGA..3'
(SEQ ID NO:127)

$$T + Hpin \rightleftharpoons T\_Hpin$$
$$Tmut + Hpin \rightleftharpoons Tmut\_Hpin$$

ULTRASPECIFIC RIBOREGULATORS HAVING ROBUST SINGLE-NUCLEOTIDE SPECIFICITY AND IN VITRO AND IN VIVO USES THEREOF

CROSS-REFERENCE TO RELATED APPLICATIONS

This application is a divisional of U.S. application Ser. No. 16/322,719, filed Feb. 1, 2019, which represents the national stage entry of PCT International Application No. PCT/US2017/044810, filed on Aug. 1, 2017, and claims priority to U.S. Provisional Application No. 62/369,298, filed Aug. 1, 2016, each of which is incorporated by reference herein as if set forth in its entirety.

STATEMENT REGARDING FEDERALLY SPONSORED RESEARCH

Not applicable.

SEQUENCE LISTING

A Sequence Listing accompanies this application and is submitted as an xml file of the sequence listing named "112624.01400.xml" which is 156,706 bytes in size and was created on Aug. 9, 2023. The sequence listing is electronically submitted via Patent Center with the application and is incorporated herein by reference in its entirety.

BACKGROUND

Synthetic biology is an emerging discipline that has great potential to respond to global pandemics. The increasing ability of synthetic biologists to repurpose and engineer natural biological components for practical applications has led to new opportunities for molecular diagnostics. Riboregulators have found utility in synthetic biology arts for regulation of bacterial responses and to probe gene regulatory networks.

Detection of single nucleotide polymorphisms is a longstanding challenge in the field of synthetic biology and for nucleic acid detection in vivo and in vitro. Generally, riboregulators contain two canonical domains, a sensor domain and an effector domain, that respond to a signal nucleic acid by binding to complementary nucleic acid strands. Since binding is based on base-pairing, riboregulators can be tailored to differentiate and respond to individual genetic sequences and combinations thereof. Despite their excellent performance in both dynamic range and orthogonality, there remains a need in the art for improved riboregulators that are capable of distinguishing single nucleotide variants (SNVs).

BRIEF SUMMARY

In a first aspect, provided herein is an ultraspecific riboregulator. Preferably, the ultraspecific riboregulator is a synthetic nucleic acid molecule comprising a fully or partially double-stranded stem domain; a loop domain; a ribosomal binding site; a start codon; a toehold sequence; a docking domain; a spacer domain between the toehold sequence and the docking domain; and a coding sequence. The toehold sequence can have a length of 3, 4, 5, or 6 nucleotides. The toehold sequence can have a length of 0 nucleotides. The stem domain can comprise the start codon. The start codon can be a 3-nucleotide region of non-complementarity. In some cases, the loop domain further comprises the start codon. In some cases, the location of the ribosomal binding site is selected from the group consisting of the loop domain, the stem domain, and combinations thereof. In some cases, the stem domain can comprise part or all of the ribosomal binding site. In some cases, the docking and spacer domain are not present and loop domain further comprises the start codon. The coding domain can encode a reporter protein.

In another aspect, provided herein is an ultraspecific riboregulator comprising a bimolecular RNA complex comprising (a) a first RNA comprising, in a 5' to 3' direction, a ribosomal binding site, start codon, sensor binding region, and a coding domain; and (b) a second RNA partially bound to the first RNA at the sensor binding region and has partial or full complementarity with a target RNA sequence. The coding domain can encode a reporter protein. The fully or partially bound toehold sequence can be located at the 3' end of the second RNA. The fully or partially bound toehold sequence can be located at the 5' end of the second RNA.

In a further aspect, provided herein is a method for detecting at least one specific RNA molecule in a sample, the method comprising: contacting the ultraspecific riboregulator as provided herein to the sample, whereby, if present in the sample, the specific RNA molecule will bind to the toehold sequence and displace the target sensing region of the ultraspecific riboregulator; and detecting expression of the encoded reporter protein, wherein detectable reporter protein expression indicates the presence of the specific RNA in the sample. The specific RNA molecule can be selected from the group consisting of a messenger RNA (mRNA) molecule, microRNA, small interfering RNA (siRNA), antisense RNA, non-coding RNA, mRNA splice variant, an RNA with chemically modified bases and an RNA with non-canonical bases. The sample can be a biological sample. Detecting said specific RNA molecule can be a positive indicator of a presence of a microorganism, pathogen, mutation, or gene in said sample. Detecting said specific RNA molecule can be a negative indicator of a presence of a microorganism, pathogen, or gene in said sample. The gene can comprise one or more mutations relative to another gene.

In a further aspect, provided herein is an ultraspecific riboregulator wherein the riboregulator is a synthetic nucleic acid molecule comprising a fully or partially double-stranded stem domain; a loop domain; a ribosomal binding site; a start codon; a toehold sequence; and a coding sequence. The toehold sequence can have a length of 3, 4, 5, 6, 7, or 8 nucleotides. The toehold sequence can have a length greater than 8 nucleotides. The location of the ribosomal binding site is selected from the group consisting of the loop domain, the stem domain, and combinations thereof. The ribosomal binding site can be wholly or partially within the stem domain and the loop domain comprises the start codon. The loop domain comprises the start codon.

The foregoing and other advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The present invention will be better understood and features, aspects, and advantages other than those set forth above will become apparent when consideration is given to the following detailed description thereof. Such detailed description makes reference to the following drawings, wherein.

| Genes | Riboregulator SEQ ID NO: | Wild-Type Target SEQ ID NO: | SNP Target SEQ ID NO: |
|---|---|---|---|
| HIV-Q151M | 8 | 9 | 10 |
| HIV-K65R | 11 | 12 | 13 |
| K13-I543T | 14 | 15 | 16 |
| K13-Y493H | 17 | 18 | 19 |
| KRAS-G12D | 20 | 21 | 22 |
| KRAS-G13D | 23 | 24 | 25 |
| RpoB-D531L | 26 | 27 | 28 |
| RpoB-T526Y | 29 | 30 | 31 |
| RpoB-G516V | 32 | 33 | 34 |
| EGFR-M858R | 35 | 36 | 37 |
| EGFR-G719A | 38 | 39 | 40 |
| HFE-C282Y | 41 | 42 | 43 |
| HFE-H63D | 44 | 45 | 46 |
| KatG-S315T | 47 | 48 | 49 |
| BRAF-V600E | 50 | 51 | 52 |
| BRCA1-P871L | 53 | 54 | 55 |
| BRCA2-N372H | 56 | 57 | 58 |

FIGS. 14A-14D demonstrates experimental verification of paper based gene mutation detection based on the ultraspecific riboregulator design shown in FIG. 1 generated for different virus strains and SNP targets. (A) The target region of three Zika virus strains originating from Arica (Af), the Americas (Am), and Asia (As). The sequence differences are indicated by the bold underlined bases. SEQ ID NOs:60, 62, and 64 represent full length SNP targets of Af, Am, and As strains, respectively. (B, C) The fluorescence (B) and colorimetric (C) readouts from a test in which the three riboregulators for each Zika strain were exposed to target RNAs from the three strains. SEQ ID NOs:59, 61, and 63 represent the sequences of the riboregulators used for the GFP output experiments for the Af, Am, and As strains, respectively. SEQ ID NOs:65, 66, 67 represent the sequences of the riboregulators used for the colorimetric lacZ output experiments for the Af, Am, and As strains, respectively. Only tests along diagonal shows significant signal change, corresponding to sensors activating only against their cognate targets. The color of the reactions have been adapted to gray scale. (D) Paper-based colorimetric detection of three disease-associated SNPs: BRCA1 P871L mutation (riboregulator of SEQ ID NO:68), BRCA2 N372H mutation (riboregulator of SEQ ID NO:69), and the HIV reverse transcriptase M184V mutation (riboregulator of SEQ ID NO:5).

Figures 15A, 15B:
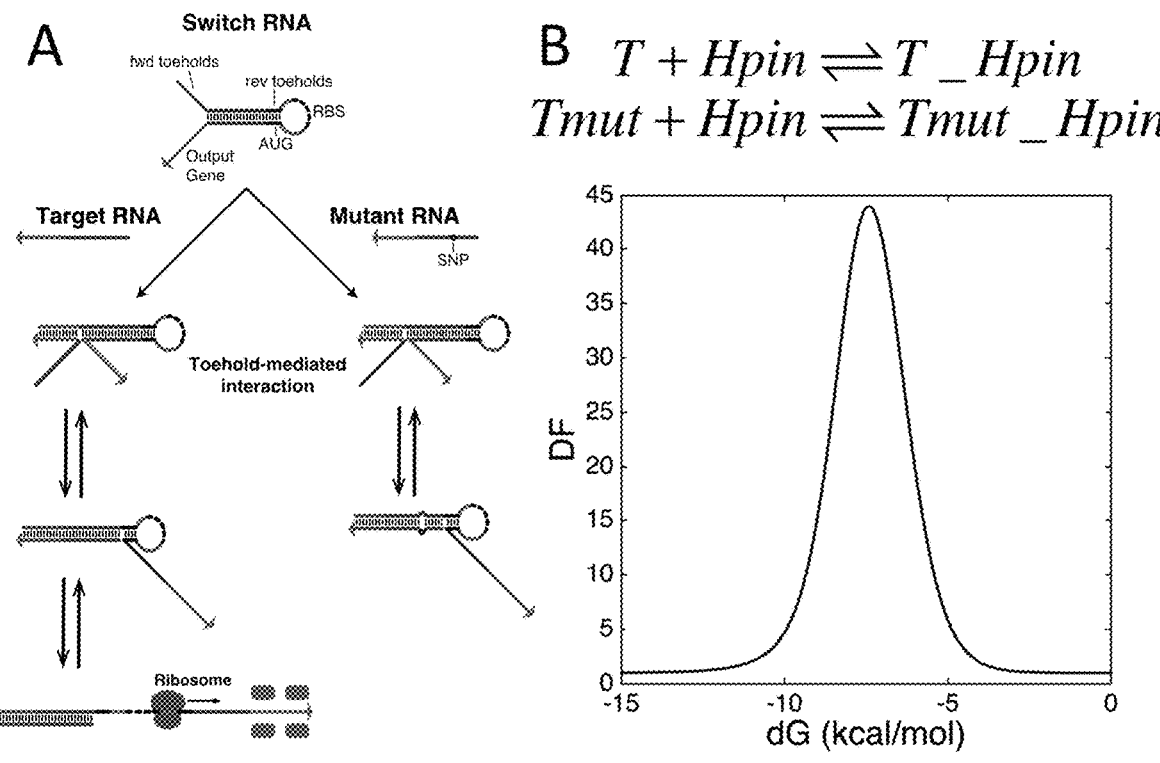

FIGS. 15A-15B illustrates (A) the principle of the engineered ultraspecific riboregulator without a docking region. (B) The relationship between the differentiation factor and reaction energy of the WT target RNA and the switch RNA is plotted.

Figure 16:
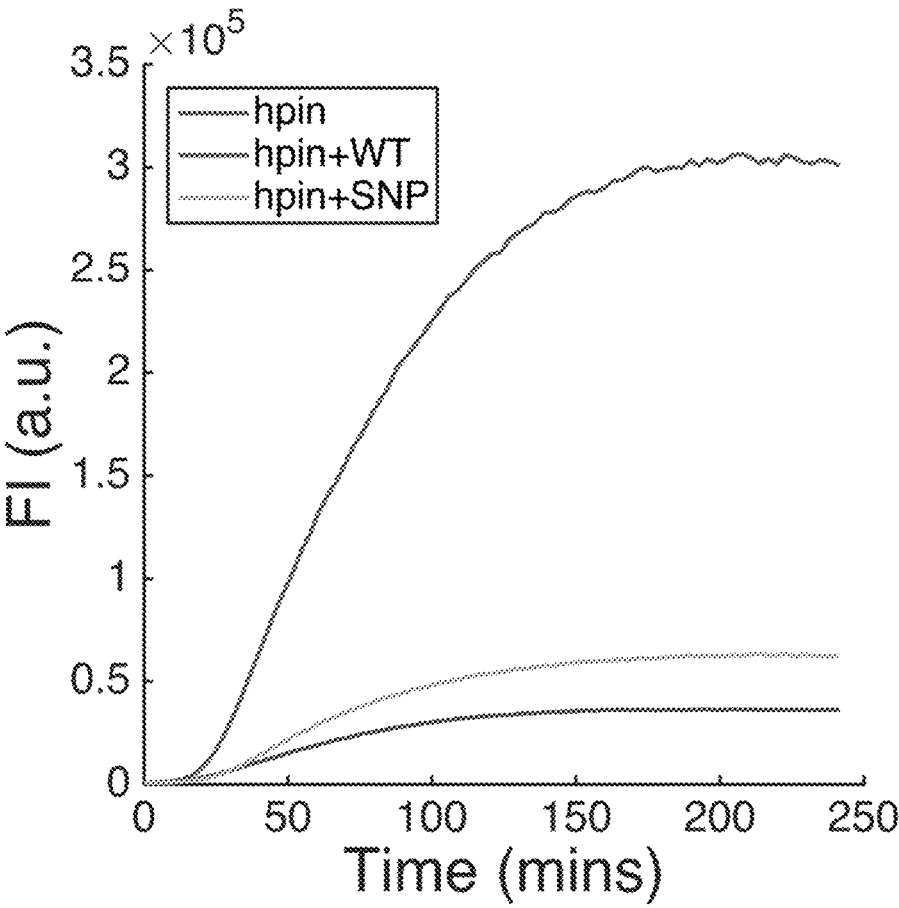

FIG. 16 demonstrates experimental verification of the ultraspecific riboregulator without docking site shown in FIG. 15A to discriminate SNP targets from wide type targets. The encoded protein is green fluorescence protein and the riboregulator activates within 1 hour.

Figure 17A:
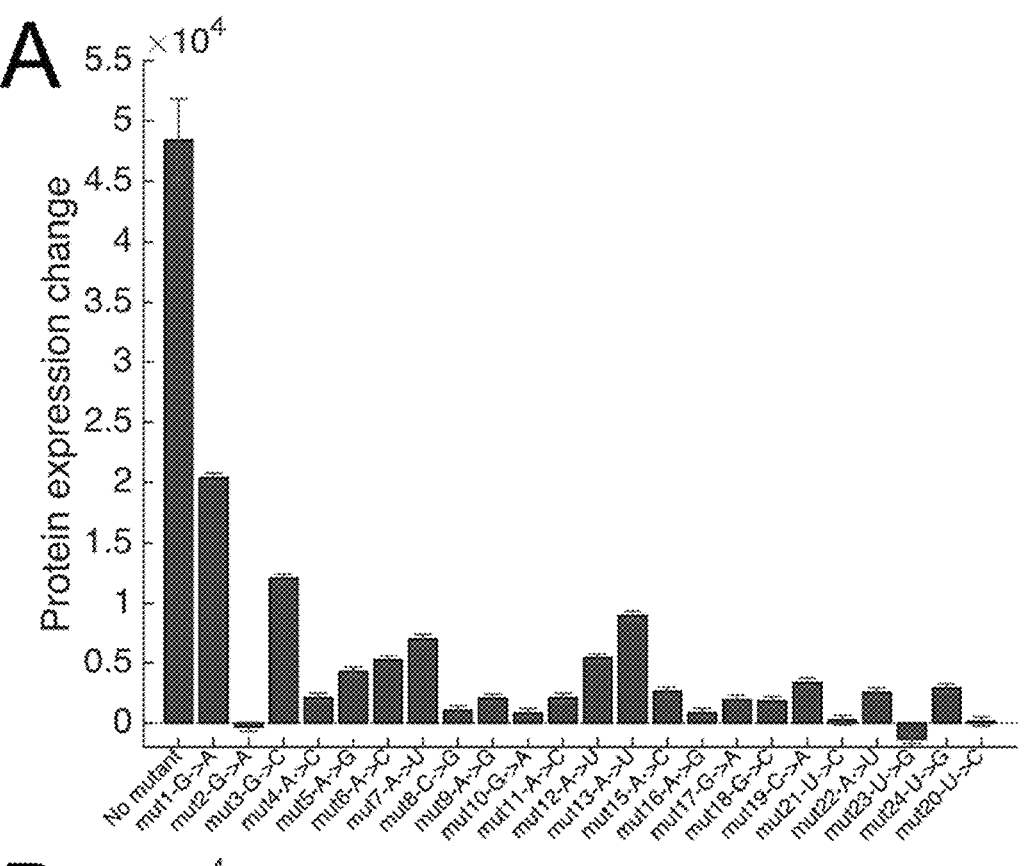
Figure 17B:
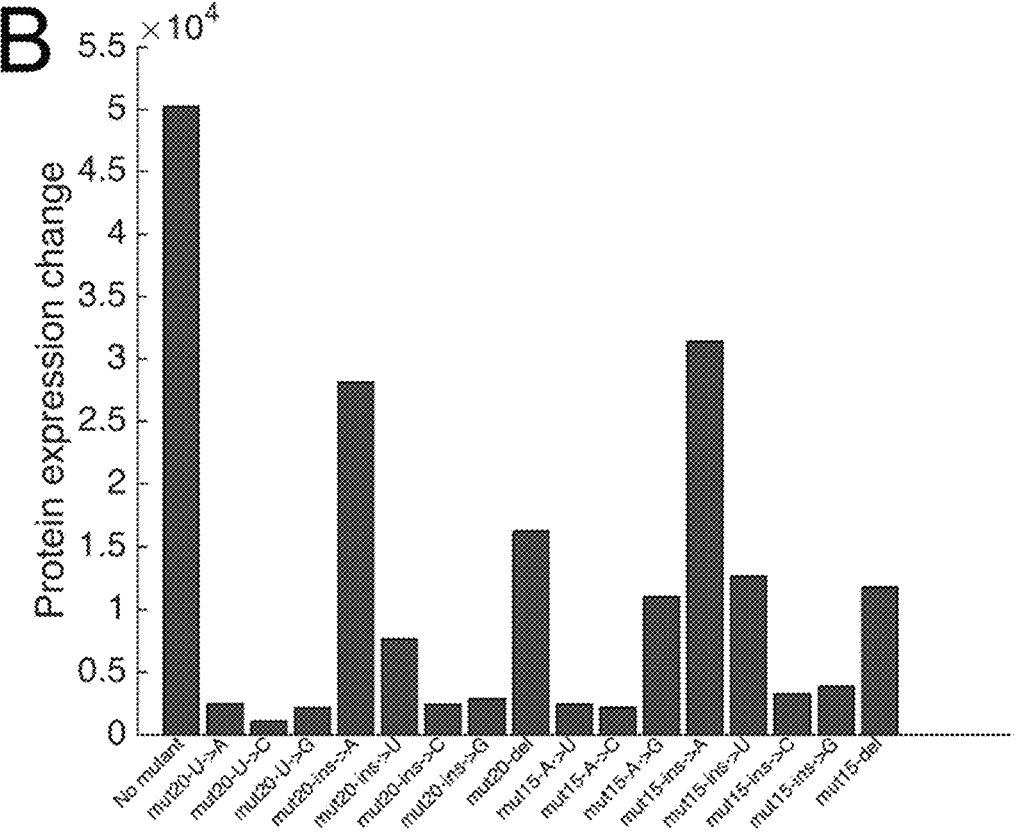

FIGS. 17A-17B show systematic studies of SNP detection in vitro using ultraspecific riboregulators lacking docking sites. (A) Plot of GFP expression for the perfect target ("no mutant") compared to a series of mutant targets featuring point mutations at different locations. All mutated targets show significantly decreased expression compared to the perfect target. (B) Plot of GFP expression for the perfect target ("no mutant") compared to mutated targets modified with substituted bases, insertions, and deletions at positions 15 and 20 from the 5' end of the target RNA.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

The methods and systems provided herein are based at least in part on the inventors' development of an ultraspecific riboregulator that is capable of differentiating variations down to a single base in a stretch of target RNA both in vivo and in vitro. The designs of these ultraspecific riboregulators utilize a novel mechanism that enables a single nucleotide change in the target RNA to cause a substantial thermodynamic penalty to prevent activation of the riboregulator. Thus, the riboregulator can only be turned on when it binds to a target RNA with the perfect sequence. Single nucleotide variants (SNVs) of target RNAs do not elicit a response from the riboregulator and provide near background expression levels. Also described herein is an riboregulator system having specificity to detect RNAs with the modified base $N^6$-methyladenosine ($m^6A$), the most common RNA modification observed in mRNAs and a crucial player in our still evolving understanding of the epitranscriptome. The ability of these riboregulators to reliably detect single-base changes in RNAs and their predicted specificity for chemically modified nucleic acids suggests far reaching implications for these systems as both critical tools for studying cell biology and as diagnostic devices for extremely precise and personalized detection of disease.

For purposes of convenience in the description, references to nucleic acid elements such as start codons, ribosomal binding site, 5' UTR, stem-loop, etc., may refer to either the RNA form or to the DNA form (i.e., to a DNA molecule that provides a template for transcription of the RNA). Similarly, when reference is made to modifying an RNA (e.g., by inserting an element such as a cis-repressive sequence) into the RNA, it is to be understood that the modification is generally accomplished by engineering the appropriate modification to a DNA molecule that provides a template for transcription of the RNA.

Accordingly, in a first aspect, provided herein is an ultraspecific riboregulator. As used herein, the term "ultraspecific riboregulator" refers to a regulator of gene expression, configured to repress or activate translation of an open reading frame, and thus repress or activate production of a protein, only upon recognition of a target RNA with the exact sequence with single nucleotide specificity. Generally, riboregulators contain two canonical domains, a sensor domain and an effector domain, that respond to a signal nucleic acid by binding to complementary nucleic acid strands. Since binding is based on base-pairing, riboregulators can be tailored to differentiate and respond to individual genetic sequences and combinations thereof. As described herein, the methods of this invention provide single-base discrimination.

Ultraspecific riboregulators provided herein are synthetic nucleic acid molecules comprising a fully or partially double-stranded stem domain; a loop domain comprising a ribosomal binding site; a start (initiation) codon; a toehold sequence; a docking domain; a spacer domain between the toehold sequence and the docking domain; and a coding sequence. In some cases, the loop domain comprises the start codon. In other cases, the start codon is located in the fully or partially double-stranded stem domain. In some cases, the ribosomal binding site is located fully or partially in the double stranded stem domain. These riboregulators may contain two different toehold domains: a first or forward toehold that the target RNA hybridizes with as it is activating the riboregulator, and a second or reverse toehold that is initially base paired at the top of the stem of the riboregulator but becomes unpaired once the riboregulator activates. In general, the thermodynamic free energy of binding for the first and second toehold sequences are designed to be very close to one another. In some cases, the length of the first and second toehold sequences can be reduced to zero to satisfy this free energy requirement.

As used herein, the terms "synthetic" and "engineered" are used interchangeably and refer to a non-naturally occurring nucleic acid molecule that has been created or modified by the hand of man (e.g., using recombinant DNA technology) or is derived from such a molecule (e.g., by transcription, translation, etc.). A nucleic acid molecule may be similar in sequence to a naturally occurring nucleic acid but typically contains at least one artificially created insertion, deletion, inversion, or substitution relative to the sequence found in its naturally occurring counterpart. A cell that contains an engineered nucleic acid is considered to be an engineered cell.

Referring to FIG. 1, there are four main differences in the design of ultraspecific riboregulators compared with a conventional toehold switch riboregulator. First, a docking region is designed to bring the target ("trigger") RNA and switch RNA together through a very strongly favorable thermodynamic reaction. The docking domain needs to be sufficiently long such that it is very thermodynamically favorable at typical reaction temperatures. In some embodiments, the docking domain is 20 nucleotides (nts). In some embodiments, the docking domain is 15 nucleotides or more. Upon docking of the target ("trigger") RNA to the switch RNA, the two RNAs are essentially irreversibly associated with one another at the temperature of our typical reactions (37° C. in most cases with a potential range from about 30° C. to about 42° C.). Thus, all subsequent interactions between the two RNAs are effectively intramolecular competitive reactions.

Figures 1A, 1B, 1C:
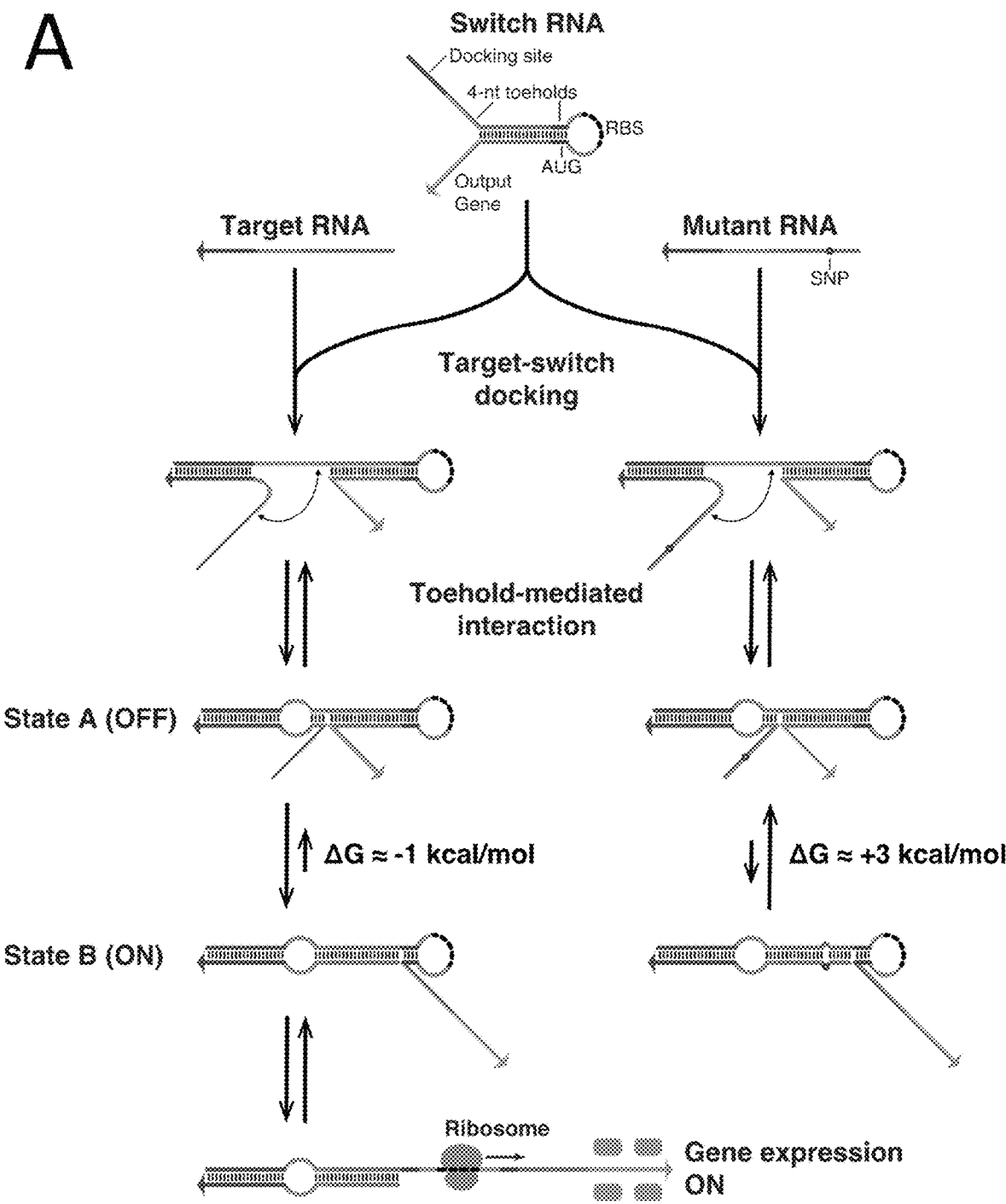
FIGS. 1A-1C illustrate energy driven design of exemplary ultraspecific riboregulators. (A) The switch RNA is assembled from a series domains of docking, bulge, forward toehold, branch migration, reverse toehold, hairpin loop, and output gene. The ribosome binding site (RBS) is put in the hairpin loop region. The start codon can be put either the stem or the loop region. The function of docking region allows both the wide-type (WT) and mutated target RNA to bind to the switch RNA to form a quasi-single molecule. The bulge region is designed to form a ~20-nt bulge to compensate for the entropy contribution of hairpin loop. The forward and reverse toeholds are used to initiate a forward and reverse branch migration to change the ON-OFF state of the riboregulators. The energy difference between the two states can be controlled by varying the toehold strength. Comparing the single nucleotide variant (SNV) to WT, a single nucleotide usually can have 4 kcal/mol energy penalty to the transition from ON to OFF state. When the target nucleic acid has no mutation(s), the free energy difference between the OFF state and ON state of the target-switch complex is engineered to be −1 kcal/mol. Thus, the target-switch complex is thermodynamically favored to enter an ON state configuration (state B and active state below) and produce an output reporter protein. In the presence of a target with one mutation, the free energy difference increases to +3 kcal/mol, which indicates the complex is strongly thermodynamically favored to adopt the OFF state and prevent reporter gene expression. (B) The equations show that the distribution between the OFF state and ON state follows the Boltzman distribution. The discrimination performance between WT and SNV target RNAs is defined as differentiation factor (Df) and can be calculated by division. (C) Plot of Df versus reaction energy calculated between the WT target RNA and the switch RNA.

Second, the switch RNA has a toehold domain that is separated from the docking site by a spacer. In example systems described herein, the spacer domains are 10 nts in the riboregulator and they are paired with a corresponding 10-nt non-hybridized spacer region in the target RNA (see FIG. 1A). In general, the spacers are designed to be about half the size of the loop domain (20 nts) so that dissolution of the loop domain during activation is matched by the formation of a bulge of overall similar size between riboregulator (10-nt spacer) and target RNA (10-nt spacer). From these considerations, in some embodiments, the spacer would range from about 5 nts to up to around 20 nts. The lengths of the spacers in the riboregulator and the target RNA do not need to be equal. Referring to FIG. 1, the spacer region is located between the docking site and the 4-nt toehold domain. When the target RNA binds to the docking site and the toehold domain, a region of non-complementarity ("bulge") of 10 nts is formed via the spacer region. This large bulge aims to provide an entropic contribution for the strand displacement reaction that balances that of the hairpin loop if the switch is activated and the hairpin opens. A "hairpin" or "hairpin structure" refers to an intramolecular structure of a nucleic acid sequence at the chosen assay temperature mediated by hybridization of complementary sequences at the 5'- and the 3'-end of the nucleic acid sequence. As used herein, the term "non-complementarity" refers to refers to an entity in a double stranded region of an RNA composition (wherein the double strand nature of the RNA composition may arise from intramolecular hybridization within one RNA molecule and/or arise from intermolecular hybridization between two RNA molecules) that comprises non-complementary nucleotides between the two strands of the double stranded region. Thus, the region may be defined as a region of non-complementary nucleotides flanked by regions of double stranded RNA. The terms "bubble" or "bulge" may also be used for the term "region of non-complementarity." It will be understood that the terms "bubble" and "bulge" imply no specific shape of said region, although in some embodiments it is shaped as a bubble.

Third, the toehold sequence of the switch RNA is made to be very short, 4 nts in the implementation shown in FIG. 1. Such short toeholds have previously been demonstrated to be ineffective for activating toehold switches, since they do not provide sufficient binding energy to reliably initiate trigger-switch binding in vivo. By establishing a quasi-unimolecular trigger-switch complex through the docking site, we effectively co-localize the short toehold and the complementary domain of the trigger thus promoting a toehold-mediated strand-displacement reaction that would be very unfavorable in an equivalent bimolecular reaction. In some cases, as depicted in FIG. 6A, the toehold domain is 0 nucleotides and the start codon is located within the loop region of the hairpin structure.

Fourth, the target is preferably not fully complementary to the stem of the hairpin, but leaves a few nucleotides at the top of the hairpin undisturbed to serve as a balancing second, or reverse, toehold for reverse strand displacement by the hairpin itself. This second toehold has the same length and/or binding energy of the first toehold. In the design depicted in FIG. 1, the second toehold contains the start codon of the output gene and the loop region contains the ribosomal binding site (RBS). In other designs, the loop can contain both the RBS and the start codon, enabling the second toehold to adopt an arbitrary sequence. In other designs, the loop can contain the start codon and part or all of the RBS can be included in the stem. Through this carefully balanced riboregulator design, competition between forward and reverse strand displacement will reach an equilibrium state. If only the initial OFF state and final ON state are considered (state A and state B, respectively, in FIG. 1), the equilibrium between these two states is determined by their free energy difference, designed to be about −1 kcal/mol. Therefore, the equilibrium slightly favors the ON state. If any base in the target region is mutated, each mismatch in the double stranded region of ON state will add an energy penalty of about 4 kcal/mol to the equilibrium. The energy difference between initial OFF state and final ON state is about 3 kcal/mol, which is very positive such that the equilibrium will extensively move toward OFF state. Accordingly, in the presence of a target with one mutation, the free energy difference increases to +3 kcal/mol and the complex is strongly thermodynamically favored to adopt the OFF state and prevent gene expression. For the perfect (i.e., having no mutations) target RNA, the favored state B configuration will transition to a fully open form with an exposed RBS and start codon enabling efficient translation of the output gene. This final transition occurs because the second toehold (red domain in FIG. 1) is short enough for it to unwind spontaneously at typical reaction temperatures.

Figures 6A, 6B, 6C, 6D, 6E:
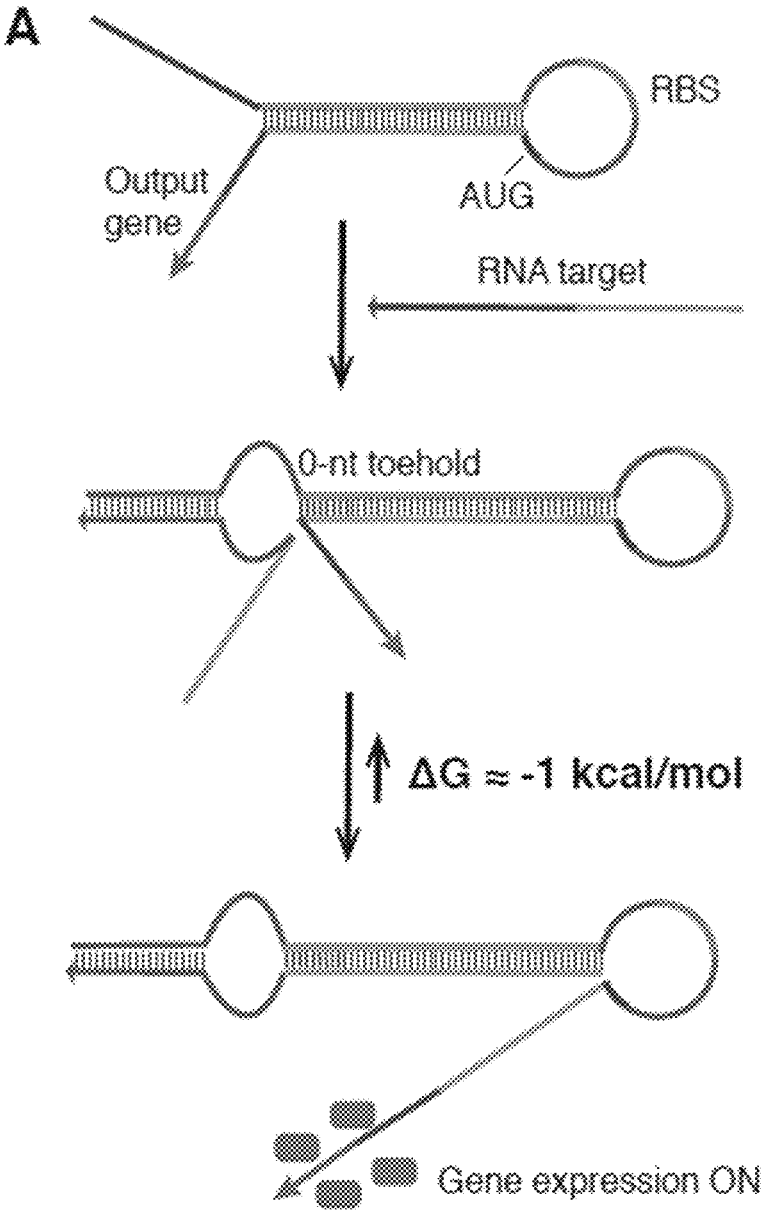
FIGS. 6A-6E illustrate alternative ultraspecific riboregulator designs. (A) A sequence-independent ultraspecific riboregulator with 0-nt toeholds based on initial design in FIG. 1. This riboregulator has the start codon and RBS within the loop region. Although the toeholds are removed from the design, transient disruption of the base pairs at the bottom of the stem will enable strand displacement to occur and activation of the switch only for perfect target RNAs. (B) A remote-toehold-based riboregulator with improved sequence independence. In this design, the RBS is in the loop region and AUG starting codon is kept as a 3-nt bulge. The 6-nt stem between bulge and loop is used as toehold for the backward displacement reaction. The forward displacement reaction makes use of a 6-nt toehold and a corresponding 3-nt bulge. (C, D) These riboregulators contain an effector strand consisting of three regions, a translation initiation region (containing an RBS and a start codon), a sensor RNA binding region, and the reporter protein region. Reporter protein expression is repressed by a sensor RNA strand that is used to detect the target RNA and that binds to the effector RNA downstream of the start codon. In the presence of RNA target, this sensor strand will bind through its toehold to the RNA target and the ensuing branch migration will release the sensor strand from the effector. The newly freed effector RNA coding sequence in turn enables reporter protein expression. The toehold region can be positioned on the 3' end (C), 5' end (D), or both ends of the blocking RNA. Secondary toeholds in the sensor RNA can be used to balance toehold binding with the target to provide SNP-specific detection. (E) Illustration of a self-cleaving ribozyme scheme for stoichiometric expression of the bimolecular riboregulator. A self-cleaving ribozyme inserted upstream of the RBS in the loop region an RNA transcript. This ribozyme cleaves, leaving a bimolecular riboregulator with a 1:1 ratio between the blocking strand and the expression strand.

Referring to FIGS. 6C-6D, another embodiment of an ultraspecific riboregulator comprises a synthetic nucleic acid molecule (e.g., RNA) comprising a start codon (translation initiation region), a target sensing region comprising a fully or partially bound toehold sequence, and a coding domain encoding a reporter protein, wherein the ribosomal binding site and start codon are located 5' to the target sensing region, wherein the coding domain is located 3' to the target sensing region. As shown in FIG. 6C, the fully or partially bound toehold sequence can be located at the 3' end of the target sensing region. Alternatively, as shown in FIG. 6D, the fully or partially bound toehold sequence can be located at the 5' end of the target sensing region.

As used herein, the terms "gene product" and "expression product" generally refer to an RNA transcribed from the gene or a polypeptide encoded by an RNA transcribed from the gene. Thus a regulatory element, environmental condition, stimulus, etc., that alters the level of transcription or the stability of an RNA transcribed from a gene or alters its ability to serve as a template for translation will be said to alter expression of the gene. Similarly, a regulatory element, environmental condition, stimulus, etc., that alters the level of translation or stability of a polypeptide translated from an RNA transcribed from the gene will be said to alter expression of the gene.

In some cases, an ultraspecific riboregulator is operably linked to a reporter element (e.g., an *E. coli* lacZ reporter element encoding β-galactosidase) that is 3' to the hairpin structure. As used herein, the term "operably linked" refers to a relationship between two nucleic acid sequences wherein the production or expression of one of the nucleic acid sequences is controlled by, regulated by, modulated by, etc., the other nucleic acid sequence. Reporter proteins appropriate for the methods provided herein include, without limitation, enzymatic reporters (e.g., β-galactosidase, alkaline phosphatase, DHFR, CAT), fluorescent or chemiluminescent reporters (e.g., GFP, GFP variants, mCherry, luciferase, e.g., luciferase derived from the firefly (*Photinus pyralis*) or the sea pansy (*Renilla reniformis*) and mutants thereof), etc.

In another aspect, provided herein are methods of altering gene expression using the synthetic nucleic acid molecules described herein. In some cases, ultraspecific riboregulators can be used to regulate expression of one or more enzymes, including entire metabolic pathways. In such cases, the method includes placing one or more enzymes (e.g., each enzyme in a metabolic pathway) under control of ultraspecific riboregulators that respond to the same trigger RNA. The inventors have demonstrated that the ultraspecific riboregulators provided herein yield unexpectedly high fold-change values, often in the 100-fold range. As used herein, the terms "expressing," "expression," or "express" refer to the production of a gene product (e.g., an mRNA transcript from a nucleic acid sequence encoding thereof). As used herein, the terms "gene product" and "expression product" generally refer to an RNA transcribed from the gene or a polypeptide encoded by an RNA transcribed from the gene. Thus a regulatory element, environmental condition, stimulus, etc., that alters the level of transcription or the stability of an RNA transcribed from a gene or alters its ability to serve as a template for translation will be said to alter expression of the gene. Similarly, a regulatory element, environmental condition, stimulus, etc., that alters the level of translation or stability of a polypeptide translated from an RNA transcribed from the gene will be said to alter expression of the gene.

In another aspect, provided herein are methods for using the synthetic nucleic acids described herein. For example, provided herein is a method for detecting a target RNA in a sample, where the method comprises contacting an ultra-specific riboregulator to a sample, whereby, if present in the sample, the specific RNA will bind to the target sensing region of the ultraspecific riboregulator; and detecting expression of the encoded reporter protein, wherein detectable reporter protein expression indicates the presence of the specific RNA in the sample. To detect single nucleotide changes, the ultraspecific riboregulator is designed to include a target-sensing region having the nucleotide change(s) of interest. In such cases, detectable reporter protein expression indicates that the sample contains RNA having the nucleotide change(s) of interest in the sample. In some cases, detecting a specific RNA molecule is a positive indicator of a presence of a microorganism, pathogen, mutation, or gene in said sample. In other cases, detecting a specific RNA molecule is a negative indicator of a presence of a microorganism, pathogen, or gene in said sample.

In some cases, the specific RNA molecule is a messenger RNA (mRNA) molecule. In other cases, the specific RNA molecule is, for example, an antisense RNA, a non-protein-coding RNA (e.g., small nucleolar RNAs, microRNAs, small interfering RNAs (siRNAs)), or mRNA splice variant. The sample can be any sample comprising total RNA and/or a biological sample. The RNA molecule may also be an RNA molecule with chemically modified amino acids, such as, but not limited to, m$^6$A (N$^6$-Methyladenosine) modifications. The RNA molecule may also be an RNA molecule with non-canonical bases.

Riboregulators having specificity to single-nucleotide changes have multiple potential applications in vitro for diagnostic purposes. Integration of these riboregulators into a low-cost, portable, and stable cell-free platform, such as one described by Pardee et al., *Cell* 159:940-954 (2014) and Pardee et al., *Cell* 165:1255-1266 (2016), could enable the applications below to be realized at under $1 per test and deployed either in the field, in remote clinics, at the point of care, or even in the home.

Drug susceptibility testing of microbial pathogens: Known mutations, many of them SNPs, are associated with resistance to different antimicrobial treatments. Examples of such mutations include a range of SNPs in the K13-propeller of *Plasmodium falciparum*, which lead to artemisinin resistance in malaria; a number of SNPs in resistant strains of *Mycobacterium tuberculosis*; and SNPs conferring resistance to different antibiotics in *Staphylococcus aureus*.

Drug susceptibility and subtyping of viruses: SNPs are also useful for identification of viruses. Examples of these include the K65R mutation in HIV, which leads to intermediate/high-level resistance to tenofovir disoproxil fumarate, abacavir, stavudine, zalcitabine or didanosine therapy; R292K oseltamivir-resistant mutants of influenza A(H7/N9) (Wang et al., *Emerging Infectious Diseases* 20:847-849 (2014)); for subtyping of influenza (Wang et al., *Journal of Clinical Microbiology* 51:3324-3330 (2013)); and for specific identification of different strains of the Zika virus (Pardee et al., *Cell* 165:1255-1266 (2016)).

Detection of cancer-associated mutations from tumor and liquid biopsy samples: SNP-specific riboregulators for a panel of oncogenic mutations can be developed to enable rapid and low-cost screening for cancer. These tools can also be applied to DNA obtained from circulating nucleic acids present in easy-to-acquire (e.g., blood, urine) patient samples.

Personalized cancer diagnostics from liquid biopsies: Sequencing of cell-free DNA is emerging as a very useful approach to monitor the status of cancer treatments, for instance in patients undergoing chemotherapy. Repeated sequencing, however, remains expensive and could be replaced using sequence-specific nucleic acid sensors like those described here. Such systems could be employed for in-home use and more frequent patient testing. In silico sensor design tools in combination with patient-specific sequencing data have the potential to enable rapid development of these personalized cancer diagnostics in a matter of weeks.

Determination of identity: Detection of single-nucleotide differences can be used to identify with high confidence individuals of interest. This capability, particularly when implemented in a low-cost and portable format, could be useful for law enforcement, forensics, and as part of biometric security measures.

Nucleic acids and/or other moieties of the invention may be isolated. As used herein, "isolated" means separate from at least some of the components with which it is usually associated whether it is derived from a naturally occurring source or made synthetically, in whole or in part.

Nucleic acids and/or other moieties of the invention may be purified. As used herein, purified means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

It must be noted that as used herein and in the appended claims, the singular forms "a", "an", and "the" include plural referents unless the context clearly dictates otherwise. Thus, for example, reference to "a sample" includes a plurality of such samples and reference to "the molecule" includes reference to one or more molecules and equivalents thereof known to those skilled in the art, and so forth.

As used herein, "about" means within 5% of a stated concentration range or within 5% of a stated time frame.

The present invention has been described in terms of one or more preferred embodiments, and it should be appreciated that many equivalents, alternatives, variations, and modifications, aside from those expressly stated, are possible and within the scope of the invention. The invention will be more fully understood upon consideration of the following non-limiting Examples.

EXAMPLES

These examples demonstrate ultraspecific riboregulators and their use as critical tools for studying cell biology and as diagnostic devices for extremely precise and personalized detection of disease.

Example 1—Engineered Ultraspecific Riboregulators

Design Principles of Ultraspecific Riboregulators: Our ultraspecific riboregulators comprise a switch RNA that regulates translation of an output gene of interest, and a cognate target RNA that binds to and activates the switch RNA. The association between the switch RNA and target RNA that drives the switch from its OFF state to its ON state is dominated by Watson-Crick base pairing interactions. These interactions cause the target-switch complex to adopt a combination of base pairs that minimizes the overall free energy of the complex. Addition of one mismatch in the RNA duplex region of the target-switch complex, for instance through a point mutation in the target RNA, will impose an energy penalty of about 4 kcal/mol to the target-switch hybridization.[4] This 4 kcal/mol energy difference provides a narrow window over which a favorable association can be transformed into an unfavorable one. If the association energy that turns on the switch RNA by the perfectly complementary target is designed to be −1 kcal/mol, which is still favorable because of the negative free energy change of the reaction, a single mismatch in the target will increase the association energy to about 3 kcal/ mol, which is sufficiently positive such that the equilibrium will extensively move toward OFF state. For the perfect target RNA, the favored state B configuration will transition to a fully open form with an exposed RBS and start codon enabling efficient translation of the output gene. This final transition occurs because the second toehold is short enough for it to unwind spontaneously at typical reaction temperatures.

Figures 2A, 2B, 2C:
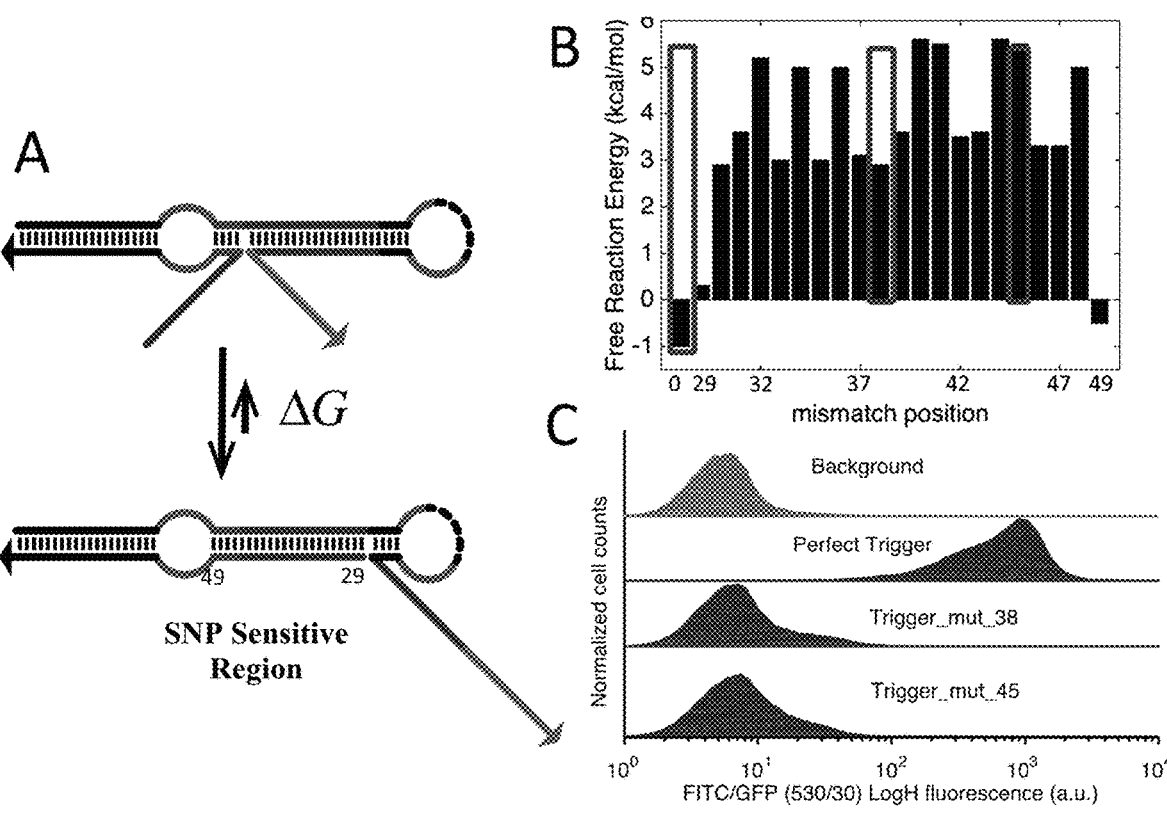
FIGS. 2A-2C present examples of ultraspecific riboregulators. (A) The SNV sensitive region encompasses the branch migration and forward toehold domains, from position 29 to 49 in the target RNA sequence. The terminator at 3' and protecting hairpin at 5' used in the target RNAs tested in vivo are not shown. The 29th position corresponds to the base that binds to the position just below the reverse toehold located in the stem of the switch RNA. (B) In silico simulated reaction energy for WT and SNP targets at each position along the SNP-sensitive region of the switch RNA. Boxes mark the target RNAs tested in panel C. Thermodynamic free energies were simulated using NUPACK. (C) Flow cytometry histograms of cellular GFP fluorescence from *E. coli* for the perfectly complementary target RNA (WT) and mutant targets (mutations at positions 38 and 45) reacting with the riboregulator.

The design of the ultraspecific riboregulators provides a SNP sensitive region in the switch RNA that spans from the first forward toehold base through to the base immediately upstream of the reverse toehold domain (FIG. 2A). FIG. 2B shows the free energy differences between state A and state B for a perfect target RNA compared to different mutated RNAs with single-point mutations spanning the SNP sensitive region of one ultraspecific riboregulator design. A mismatch position of 0 corresponds to the perfect target RNA and the remaining mismatches are specified according their position from the 5' end of the target RNA. Bases 29 through 49 correspond to the domains of the trigger RNA as shown in FIG. 1. These particular designs used trigger RNAs with hairpin regions of 28 nts added to their 5' ends to increase RNA stability for later in vivo testing; however, the hairpins are not required for successful target RNA detection. While the perfect target has a −1 kcal/mol energy difference, 19 of the 21 mismatch locations provide predicted free energy differences of approximately 3 kcal/mol or more and are thus very unfavorable. Accordingly, in the presence of a target with one mutation, the free energy difference increases to +3 kcal/mol and the complex is strongly thermodynamically favored to adopt the OFF state and prevent gene expression.

In vivo component validation: The ultraspecific riboregulators were tested in E. coli BL21 star DE3 with the switch and trigger RNAs expressed from separate medium and high copy plasmids, respectively. Expression of both strands was induced using IPTG, which triggered production of both RNA species through T7 RNA polymerase. GFP was regulated by the switch and was used to characterize switch output performance via flow cytometry.

Representative flow cytometry histograms of GFP output from the perfect target and two mutant targets with single-nucleotide differences are shown in FIG. 2C. GFP fluorescence measured from cells expressing the switch and perfect cognate target shows significant difference over control constructs with non-cognate targets, while fluorescence measured from cells expressing mutant targets and switches shows nearly same level of fluorescence as cells expressing the switch with non-cognate targets.

Figure 3A:
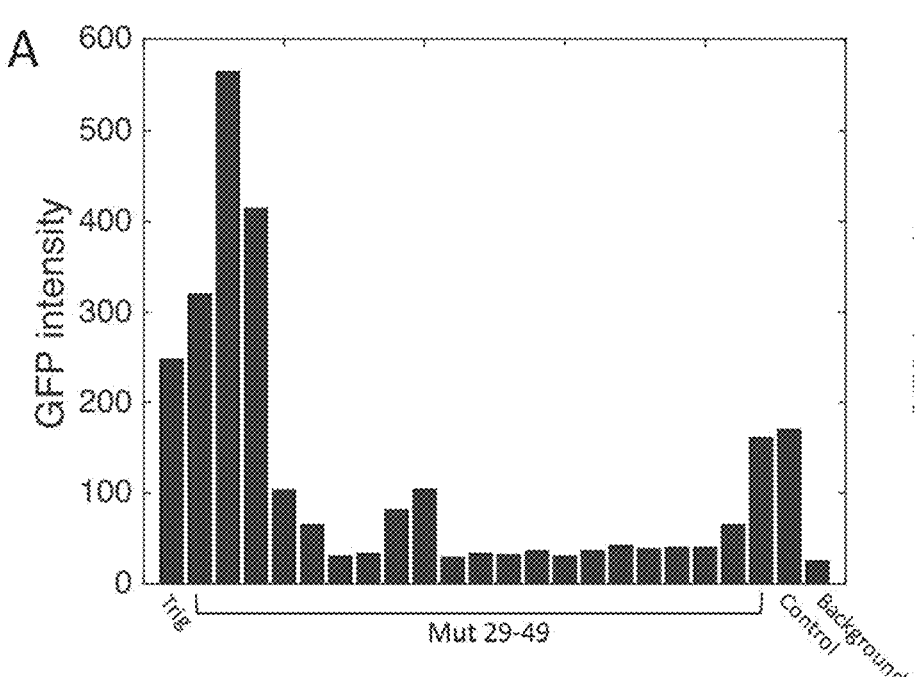
FIGS. 3A-3B present measurements of ultraspecific riboregulators operating in vitro in cell-free systems. (A) The region from position 29 to 49 shows multiple sites where mutated target RNAs are unable to activate the riboregulator and thus provide near background GFP expression levels. In other positions, such as 29 and 49, the mutated targets strongly activate this particular riboregulator; however, in practice, the SNP detection site can be designed to avoid these positions. (B) Kinetic traces of ultraspecific riboregulator activation in vitro. With the perfectly complementary target, GFP intensity increases steadily over the 4 hr measurement while GFP intensity in the case of the mut37 target, with a point mutation at position 37, remains similar to the background fluorescence measured in the absence of any target RNA.
Figure 3B:
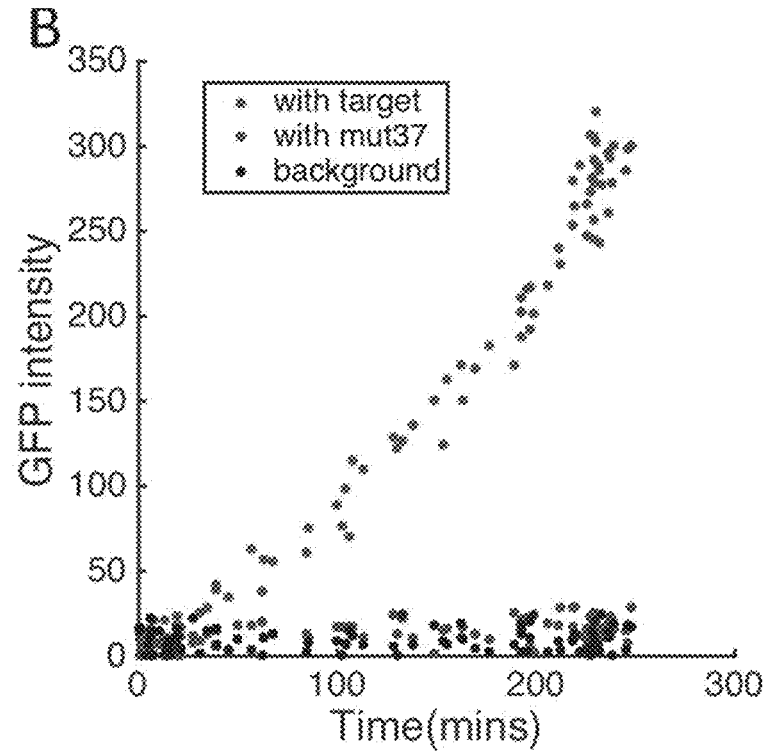

In vitro cell-free and paper based validation: After in vivo testing, we evaluated the performance of the ultraspecific riboregulator design in cell-free systems to achieve fast and sensitive response to the SNV target. In some cases, the signal resulting from the binding of perfect target and switch is much higher than that of mutant target and switch. Preferably, the signal from binding of a mutated target and switch is as low as the cell-free media background. FIG. 3A presents GFP fluorescence obtained from 21 targets with different mutation positions. At many positions, the mutant targets show significantly lower fluorescence signal compared to the perfect target. When the mutant position is at the middle of the branch migration region, the GFP signal is as low as the background level. However the mutant target is able to turn on the hairpin if the mutated nucleotide position is at the end of branch migration region. This behavior occurs because of the small kinetic trap for the forward strand displacement reaction to turn on the switch. Although this particular device has positions where mutated target RNAs show substantial and sometimes higher expression levels than the perfect target, in practice when detecting a known pathogenic RNA, it is straightforward to shift the relative binding sites of the expected SNPs so that they occur within the most sensitive regions of the switch RNA. FIG. 3B provides a time-course measurement of ultraspecific riboregulator activation in the cell-free system. This GFP-expressing sensor displays detectable fluorescence within 40 minutes of reaction and provides increasing GFP levels for the perfect trigger for the entire 4-hour measurement. In contrast, the switch RNA in the presence of a mutated trigger displays near background level GFP production throughout the kinetic trace.

Figure 4:
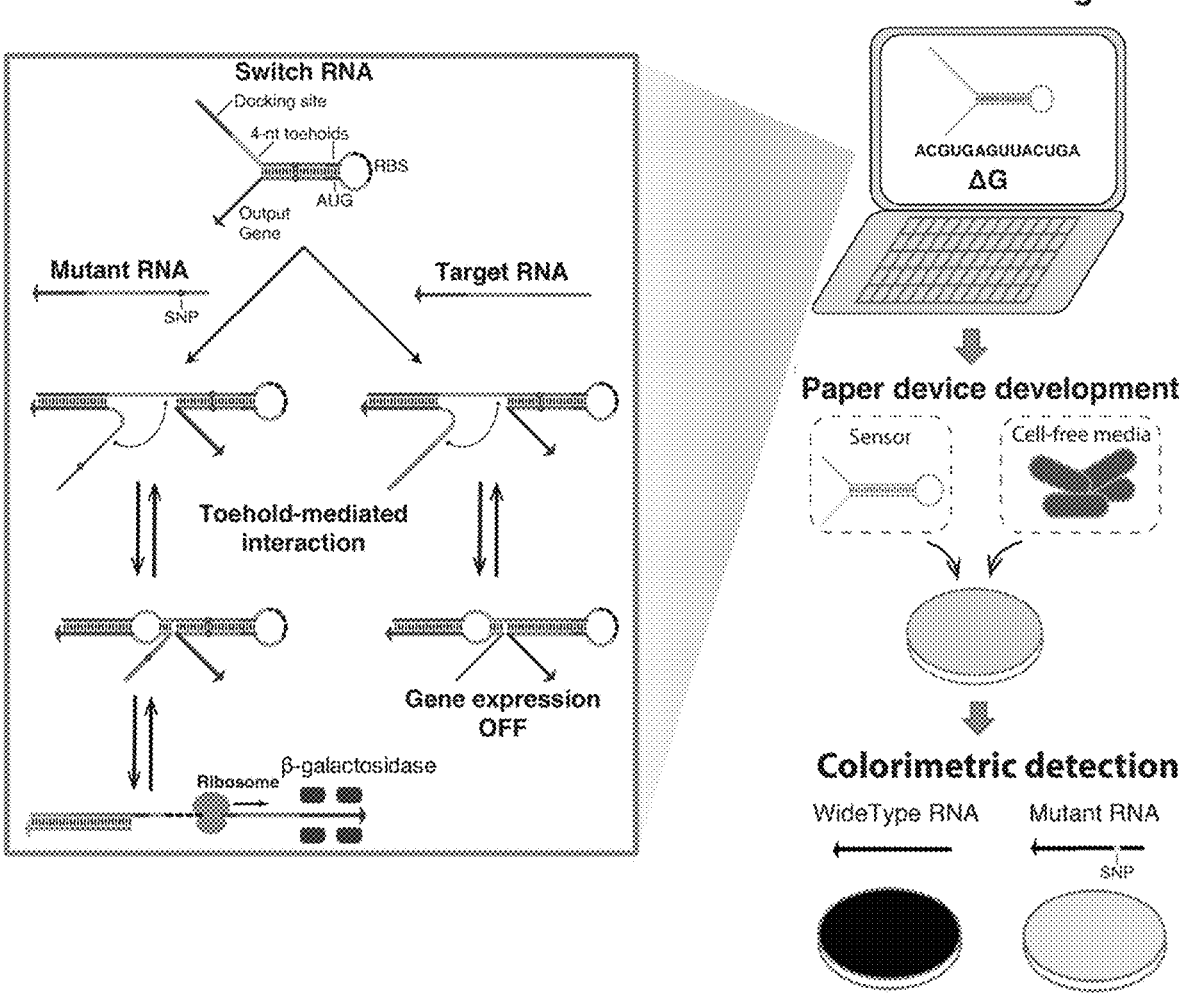
FIG. 4 illustrates visualization of a SNV target by the naked eye on paper. GFP is replaced by LacZ as the reporter protein and is able to generate an enzymatic color change that is readily detected by eye. Also illustrated is an exemplary workflow for low cost, rapid, paper-based gene mutation detection devices based on the ultraspecific riboregulators. Colorimetric detection is adapted to gray scale in FIG. 4, where expression of the reporter protein is detected in the sample having wild type RNA compared to the sample having a mutant RNA.

In another aspect, provided herein is a paper-based sensing system that allows visualization of SNV target by the naked eye in a paper strip. The toehold switch has already been shown as a powerful tool to sense the Ebola and Zika viruses in a rapid, low-cost way. Accordingly, we wanted to develop a system that is able to distinguish SNV, which is a highly desirable capability for an array of potential diagnostic purposes. From the in vivo flow cytometry and in vitro cell-free data, we observed that if the mutated nucleotide is located in the middle of target-binding region, the output protein expression levels are almost the same level as background. Thus, as shown in FIG. 4, GFP can be replaced with the enzyme β-galactosidase (LacZ), which is able to generate a dramatic enzyme-mediated color change. The illustrated reactions in FIG. 4 are shown in gray scale. In practice, LacZ cleaves the yellow substrate, chlorophenol red-β-D-galactopyranoside, embedded into the freeze-dried paper discs, to produce a pure chlorophenol red product that is visible to the naked eye. Other proteins can be incorporated into the diagnostic system for readout. Examples of potential reporters are luciferases (e.g., firefly luciferase, nanoluciferase, Renilla, Gaussia, Cypridina), which output a luminescence signal; fluorescent proteins other than GFP (e.g., mCherry, cerulean, venus, mPlum); enzymes with colorimetric substrates (e.g., β-glucuronidase, chitinases); horseradish peroxidase, which has both colorimetric and chemiluminescent substrates; proteins that can be used as intermediates in a pathway to yield a detectable output (e.g. alpha subunit of 0-galactosidase that associates with the omega subunit to yield a functional β-galactosidase enzyme, glucose oxidase that can be used in combination with horseradish peroxidase); and enzymes such as glucose oxidase that yield products that can be measured through electrochemical methods (e.g., $H_2O_2$).

Figure 5A:
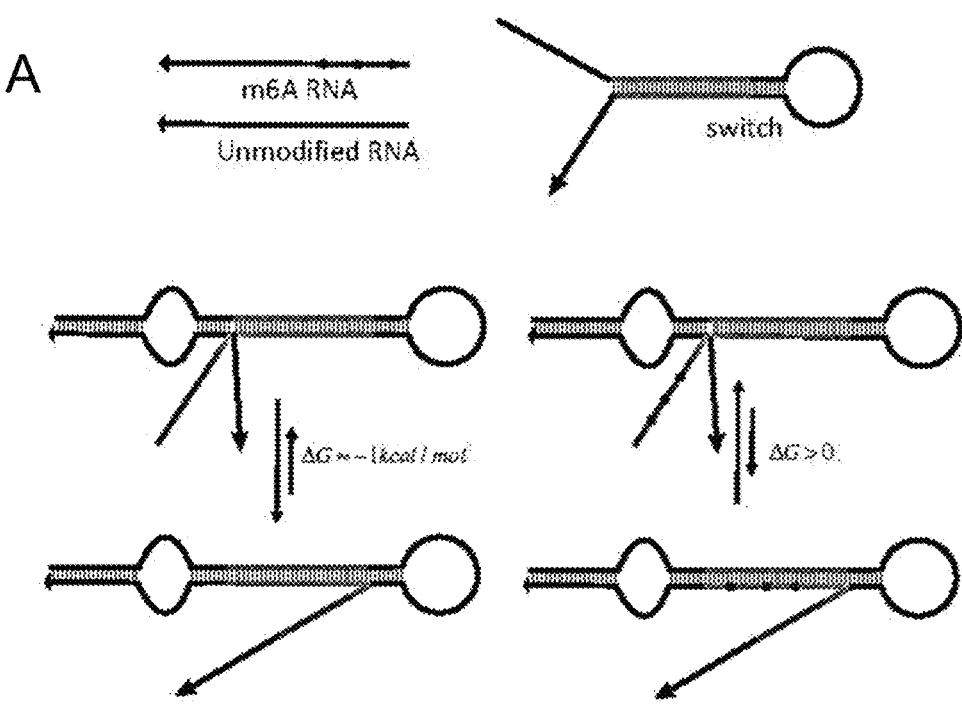
FIGS. 5A-5B present data demonstrating identification of $m^6A$ modified RNA using an ultraspecific riboregulator. (A) Schematic of the riboregulator design for an RNA with three $m^6A$ bases. (B) The theoretically predicted fold change of unmodified RNA targets versus modified RNA targets with differing numbers of $m^6A$-modified bases.
Figure 5B:
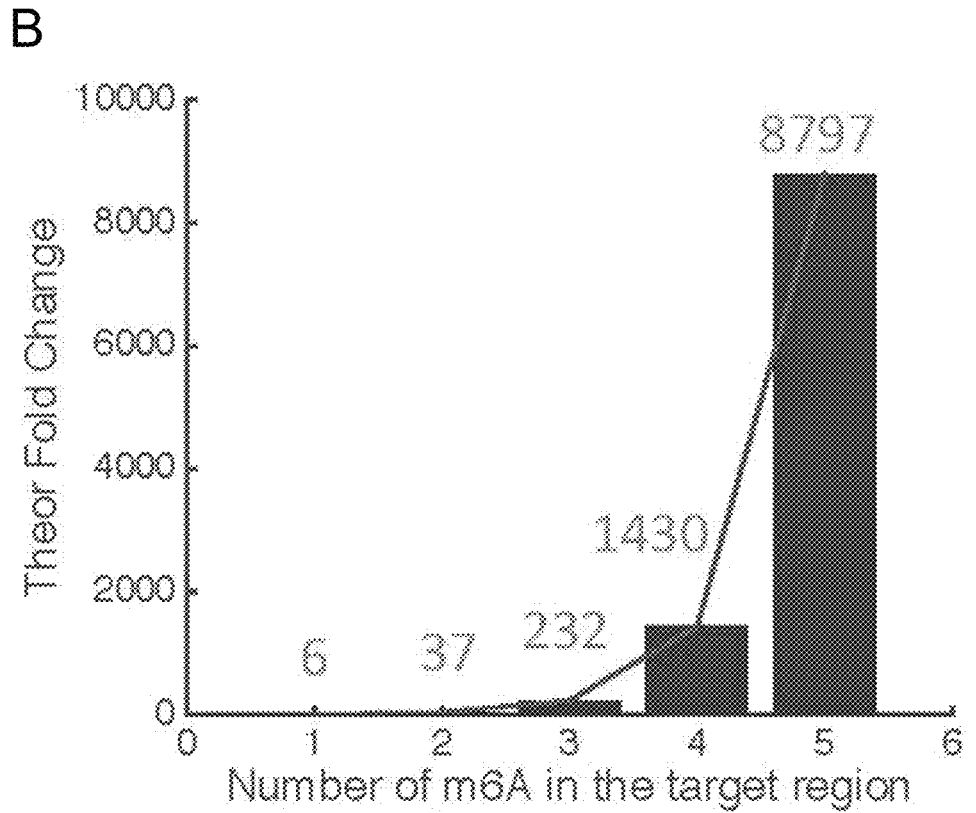

Riboregulators for Detection of Modified Bases: The ultraspecific riboregulator design is very sensitive to energetic changes in the branch migration region. Nucleic acids with chemically modified bases will influence the hybridization free energy, which affects the equilibrium between the forward the reverse strand displacement reaction and further cause different expression level of the reporter protein. Differences in expression level can be observed by flow cytometry, plate reader, or the naked eye on paper. We propose to use this concept to move beyond detection of RNA sequence and to develop riboregulators capable of detecting modified DNA and RNA bases. In particular, we focus on detection of the m[6]A modified RNA. m[6]A marks are the most abundant mRNA post-transcriptional modification and are currently the subject of considerable investigation as a result of their potentially broad role in RNA biology. A critical challenge in understanding these effects is the difficulty in detecting m[6]A modifications in endogenously expressed mRNAs. One m[6]A in a double strand RNA region, however, causes an energy penalty of about 1.125 kcal/mol based on values reported in the literature.[5] Consequently, we have designed a riboregulator with sensitivity to modified bases enabling the detection of m[6]A modified RNA target as shown in FIG. 5A. The relationship between theoretical protein expression fold change and the number of m[6]A sites is illustrated in FIG. 5B. When the number of m[6]A in the target region increases to 5, the theoretical fold change is over 8000, which demonstrates the potential of the ultraspecific riboregulators to sense m[6]A and other RNA modifications.

Although this riboregulator design will activate most strongly only for target RNAs that do not have any m[6]A modifications, it is possible to invert this behavior by having the riboregulator output a transcriptional repressor to turn off expression of a reporter, or by having the strand released upon trigger binding deactivate translation by binding to another RBS and/or start codon region. The latter RNA-RNA interaction could occur through intermolecular or intramolecular mechanisms. In addition, a less specific riboregulator could be targeted to another portion of the same target RNA to demonstrate that the RNA of interest is present in the sample by translation of one reporter. If another region of the target RNA has substantial chemical modification, a second modification-sensitive riboregulator would not translate a second reporter.

Alternative Ultraspecific Riboregulator Designs: The ultraspecific riboregulator design in FIG. 1 design has three main limitations. First, the second toehold domain of the switch RNA (adjacent to the loop domain) has some sequence dependence since it contains the start codon AUG. This constraint affects the first toehold, which must bear an energetically matched sequence, and in turn influences the potential sequences of the target RNA. Second, partial unwinding of the stem to activate the switch leads to unpredictable behavior during experimental tests, as indicated by the high expression levels observed for mutant target RNAs with mutations toward their 5' ends (FIG. 2A) despite their favorable predicted thermodynamics (FIG. 2B). Third, the range of greatest sequence specificity is limited to target regions that interact with the middle of the switch stem. Since RNA stems of extended length cannot be generated without transcriptional termination, the region in the target RNA that can be detected with SNP sensitivity is limited to approximately 25 nts depending on the specific RNA polymerase used for transcription or the chemical RNA synthesis method employed.

FIGS. 6A-6E provide schematics of three alternative ultraspecific riboregulators that address the above limitations. The design shown in FIG. 6A employs a switch RNA in which both the RBS and start codon are contained within the loop. Consequently, this design removes the AUG sequence constraint of the FIG. 1 design. In addition, the toehold regions are reduced to 0 nts in length, and are thus removed from the design entirely. The intramolecular interactions now make use of transient disruption of base pairs or "breathing" of the base pairs to enable strand invasion of the trigger RNA. Removal of the toeholds in this design also means that the system no longer has to rely on the unpredictable breathing interactions at the top of the stem, which should enable more predictable system performance and a yield a larger SNP-specific region in the switch RNA.

The design shown in FIG. 6B also eliminates sequence dependent constraints, this time by moving the AUG start codon region into a 3-nt bulge in the switch RNA. A matching 3-nt bulge is added to the 5' end of the switch RNA. In this design, the two toeholds are now comprised of the 6-nt base pairing regions adjacent to the 3-nt bulge points, and thus the forward and reverse strand-displacement reactions must proceed across the bulge region. Toeholds that employ such bulge sites are termed remote toeholds. In the presence of the perfect target RNA, unwinding of the switch RNA stem yields a stem loop with the 6-nt stem corresponding to the second toehold. This stem loop can open spontaneously and enable efficient translation of the output gene.

A pair of bimolecular toehold switch designs that can be employed for SNP detection are shown in FIGS. 6C-6D. These bimolecular designs improve target sequence independence and enable very long regions of SNP-level specificity. The switch RNA in these designs is now divided into two different strands: an effector strand, which contains an RBS, start codon, and the output gene; and a sensor strand, which is comprised of a toehold domain, a target sensing region, a secondary toehold to aid with SNP sensitivity, and can have a docking site for SNP sensitivity (not shown in FIGS. 6C-6D). Upon formation of this switch RNA complex, translation cannot occur because the blocking strand forms an extended (>20-nt) duplex that prevents the ribosome from scanning along the effector RNA. Upon expression of the target RNA, a toehold-initiated strand-displacement interaction occurs, causes the target-sensor RNA complex to be released, and enables the freed effector RNA to be actively translated. The toehold can be located on either 3' end (FIG. 6C) and/or the 5' end (FIG. 6D) of the blocking strand.

The use of a bimolecular complex for the switch RNA of the riboregulator does lead to some concerns regarding the stoichiometry and assembly yield of the complex. A high yield of the assembled complex can be obtained by expressing the sensor strand in excess of the effector strand. However, the free sensor strands produced from such a system would act as sinks to prevent the target RNAs from activating the effector RNA. In order to address these issues, it is possible to implement the ribozyme-based strategy shown in FIG. 6E. In this design, a self-cleaving ribozyme is introduced to a large loop region in a single RNA strand that contains both the sensor strand and effector strand. This self-cleaving ribozyme is placed between the sensor strand sequence and before the RBS of the effector RNA. When this RNA is transcribed, it will eventually fold into the extended hairpin shown in the left side of FIG. 6E. However, because of the length and complex secondary structure of the loop region, formation of the hairpin will not be sufficiently fast to encourage transcription termination. The resulting hairpin will then cleave into two separate molecules after cleavage by the ribozyme component to form the bimolecular switch complex. Although this riboregulator will still be active in the absence of a functional ribozyme, use of a bimolecular complex provides entropic advantages since the number of species before (effector/sensor complex+target RNA) and after (effector RNA+sensor/target complex) the reaction is conserved.

An additional design for an ultraspecific riboregulator is shown in FIG. 15A. This system is very similar to the design shown in FIG. 1, except that it does not feature a docking site for initial binding between the target RNA and the switch RNA nor does it have a spacer sequence. Although the docking site is highly advantageous for riboregulators employed in vivo, it is not an absolute requirement in less stringent conditions, such as in vitro reactions, where there are fewer active RNases, RNA binding proteins, etc., in the surrounding environment. In such situations, a riboregulator with short forward and reverse toeholds with lengths ranging from 3 to 8 nucleotides can be employed for SNP detection. The target RNA binds directly to the short forward toehold of the switch RNA and can complete a branch migration if it is perfectly complementary to the switch RNA. After this branch migration occurs, the short reverse toehold at the top of the switch RNA stem can spontaneously unwind to enable translation of the output gene. These riboregulators can have the start codon positioned within the switch stem as depicted in FIG. 15A or it can be placed within the loop along with the RBS. In other designs, the RBS or a portion thereof can be moved from the loop and into the stem. FIG. 15B shows the differentiation factor calculated for this ultraspecific riboregulator design. The differentiation factor can rise to nearly 45 for optimized reaction free energies. This mark is not as high as the nearly 200 differentiation factor of the riboregulators with docking sites; however, the docking-free design can be used for shorter target RNAs and requires less complex in silico design procedures.

In Silico Design and Selection of Ultraspecific Riboregulators

All the sequences of trigger and switch were designed and screened using NUPACK. Generally, hundreds of sequences were first generated by NUPACK and then screened by the reaction energies between perfectly complementary trigger RNAs and switch RNAs. The energy between triggers and switches with perfect complementarity was screened to be −1 kcal/mol. This slightly negative thermodynamic free energy was selected to provide an optimal degree of sequence discrimination against mutated triggers, featuring one or more point mutations. Mismatches in trigger-switch binding for the mutated triggers ensures that they produce a positive change in free energy, which prevents the mutated triggers from activating the switch.

In Vivo Verification

All the DNA sequences of trigger and switch were ordered from IDT (Integrated DNA technologies, Inc.) and assembled into plasmids using Gibson assembly. Sequence-confirmed plasmids encoding trigger and switch RNA sequences were then transformed into E. coli BL21 Star DE3. Expression of RNA triggers and switches was induced with 0.1 mM isopropyl β-D-1-thiogalactopyranoside (IPTG). Cells were then growth for an additional 3 hours and GFP expression levels measured by flow cytometry.

In Vitro Reaction in Cell-Free Expression Media

The cell-free expression media was purchased from New England Biolabs (NEB). A typical cell-free expression reaction contains 33 nM of switch DNA and 3 μM of RNA trigger. The total volume of the reaction was 7 μL containing 2.8 μL of solution A, 2.1 μL of solution B and 0.35 μL of RNase inhibitor. For a GFP-encoded switch, the rest of the volume was filled up to 7 μL by adding switch DNA, trigger RNA, and water. For a LacZ encoded switch, 0.6 mg/ml of the chlorophenol red-b-D-galactopyranoside substrate was added. After mixing of the components, the reaction solution was transferred to clear-bottom 384-well plates for signal measurement.

Engineered Riboregulators Enable Detection of Nucleic Acid Targets

Figures 7A, 7B, 7C:
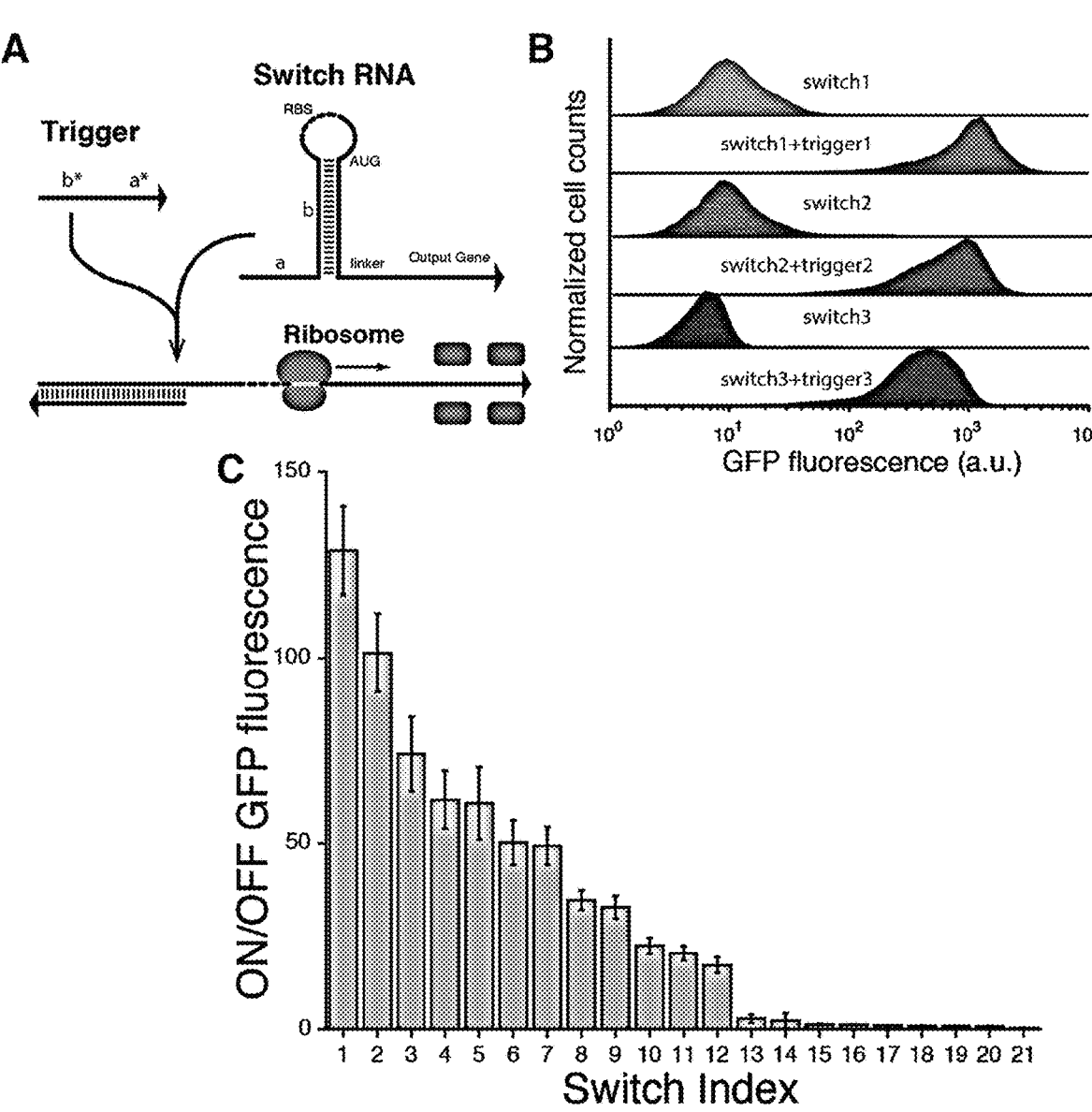
FIGS. 7A-7C present an engineered riboregulator having a ribosomal binding site (RBS) and start codon AUG in the loop region. (A) The switch RNA has a trigger hybridization region along the toehold and stem. The loop contains the ribosomal binding site and start codon. These riboregulators differ from toehold switches because their loop regions contain both the RBS and the start codon, whereas toehold switches contain only the RBS in the loop and the start codon is located within a bulge in the hairpin stem. These new engineered riboregulators do not require the bulge within the stem, alleviating some trigger sequence constraints and removing a source of leakage. (B) An in vivo experimental verification of the riboregulator design with three different riboregulators evaluated using flow cytometry. Cells expressing the switch alone show low GFP expression, while those with the trigger and switch RNA provide high GFP expression. (C) Measurements from a library of 21 different engineered riboregulators all featuring switch RNAs with loops containing both the RBS and the start codon. Over 25% of the devices provide greater than 50-fold increase in GFP expression upon detection of the target RNA.

As shown in FIGS. 7A-7C, engineered riboregulators in which the RBS and AUG are located in the loop region were designed. These riboregulators differ from toehold switches because their loop regions contain both the RBS and the start codon, whereas toehold switches contain only the RBS in the loop and the start codon is located within a bulge in the hairpin stem. These new engineered riboregulators do not require the bulge within the stem, alleviating some trigger sequence constraints and removing a source of leakage. A switch RNA with a trigger hybridization region along the toehold and stem is shown in FIG. 7A. The loop contains the ribosome binding region and start codon, like some embodiments of the ultraspecific riboregulators. However, the engineered riboregulators do not have a docking site and a spacer, and instead have an extended toehold domain used for initial binding to the target RNA. This toehold domain can range from 9 to 30 or more nucleotides. Upon activation by the target RNA, the RBS and start codon become free for ribosome binding and translation of the output gene can occur. As shown in FIG. 7B, an in vivo experiment was performed to verify the riboregulator design with three biological replicates from flow cytometry. Cells expressing the switch alone (left curves) show low GFP expression, while those with the trigger and switch RNA provide high GFP expression (right curves), thus confirming operation of this riboregulator design. We further tested a library consisting of 21 different engineered riboregulators with 15-nt toehold domains and determined their ON/OFF ratios via flow cytometry upon expression of cognate and non-cognate target RNAs (FIG. 7C). Almost 60% of the devices showed at least 10-fold ON/OFF ratio and over 25% displayed an ON/OFF ratio greater than 50-fold.

Figure 8:
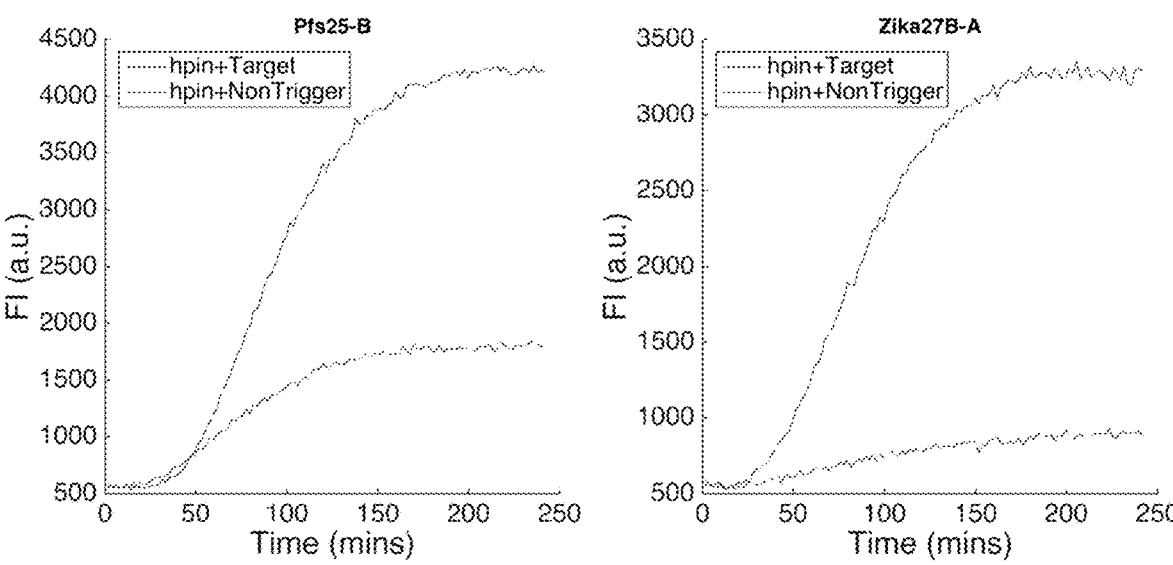
FIG. 8 demonstrates engineered riboregulators based on the design in FIG. 7A for detection of Malaria and Zika virus. (Left) Riboregulator that detects the Pfs25 gene of the malaria parasite *P. falciparum*. SEQ ID NO:1 represents the sequence of the riboregulator used. SEQ ID NO:2 represents the sequence of the wild-type target. (Right) Riboregulator that detects RNA from the Zika virus strain circulating in the Americas. SEQ ID NO:3 represents the sequence of the riboregulator used. SEQ ID NO:4 represents the sequence of the wild-type target.

Engineered riboregulators designed as described above were tested for the ability to detect specific parasite genetic material. As shown in FIG. 8, we developed engineered riboregulators capable of detecting (left) the Pfs25 gene of the malaria parasite *P. falciparum* and (right) the RNA from the Zika virus strain circulating in the Americas.

```
Pfs25 sensor (SEQ ID NO: 1):
GGGCAUUAUUUACCAUAUCAUAUCCAAGAUUACAUUUACAACAGAGGAG

AUAACGAAUGGUAAAUGUAAUCUUGGAUAUGAAACAACUAACACUAAUC

CGCAUGCGUAAAGGAGAAGAACUUUUCACUGG

Zika sensor (SEQ ID NO: 3):
GGGUUUCGCUCUAUUCUCAUCAGUUUCAUGUCCUGUGUCACUAGAGGAG

AUAACGAAUGGACACAGGACAUGAAACUGAUGUACCAACUAAACUACCC

CUCAUGCGUAAAGGAGAAGAACUUUUCACUGG
```

Design and Systematic Testing of Ultraspecific Riboregulators

Referring again to FIGS. 1A-1C, energetic driven design of ultra-specific riboregulators includes assembling a switch RNA from a series domains: docking, bulge, forward toehold, branch migration, reverse toehold, hairpin loop, and output gene. The ribosome binding site (RBS) is located in the hairpin loop region, and the starting codon can be located in either the stem region or the loop region. The function of docking region is to allow both the wild-type and mutant type target RNA to bind to form a quasi-single molecule. The bulge region is designed to form a ~20-nt bulge to compensate the entropy contribution of hairpin loop. The forward and reverse toehold are used to initiate a forward and reverse branch migration to change the ON-OFF state of the riboregulators. The energy between the transition between the two states can be controlled by varying the toehold strength. Comparing the single nucleotide variant (SNV) to WT, a single nucleotide usually has 4 kcal/mol energy penalty to the transition from ON to OFF state. The distribution between the OFF state and ON state follows the Boltzman distribution. The performance of the discrimination between WT and SNV type is defined as differentiation factor (Df) and can be calculated by division.

Figure 9:
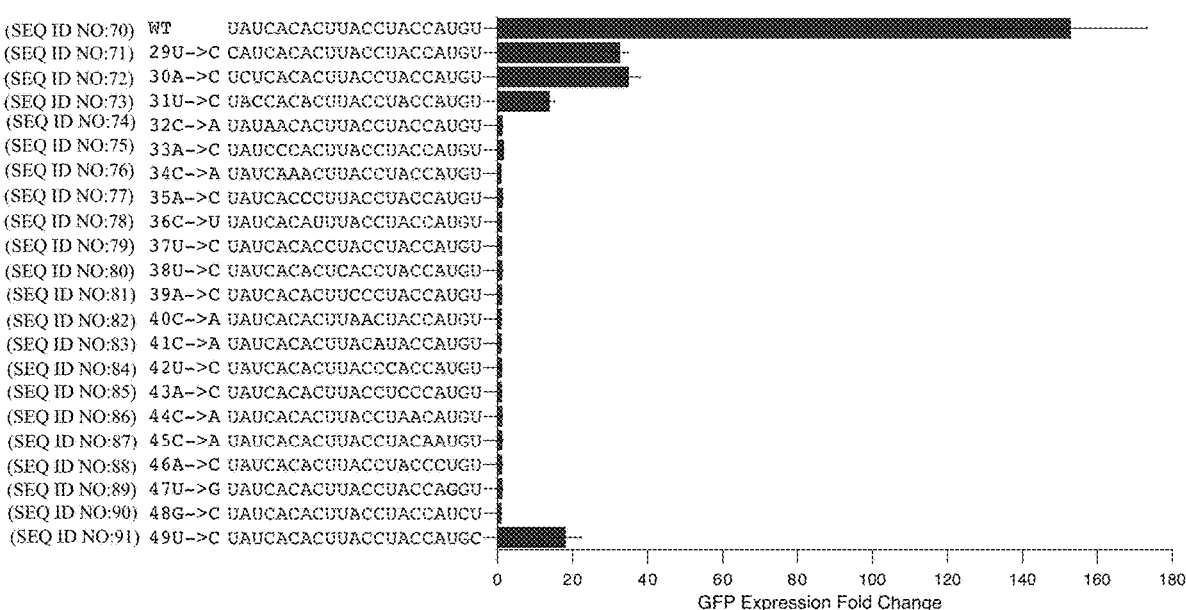
FIG. 9 demonstrates in vivo verification of SNP discrimination at each position along the SNP sensitive region for the ultraspecific riboregulator design shown in FIG. 1. All the cells with mutant type RNA triggers have significantly lower GFP expression compared with cells that have wide type RNA triggers. The positions from 32 to 48 show almost no GFP expression.
Figures 10A, 10B:
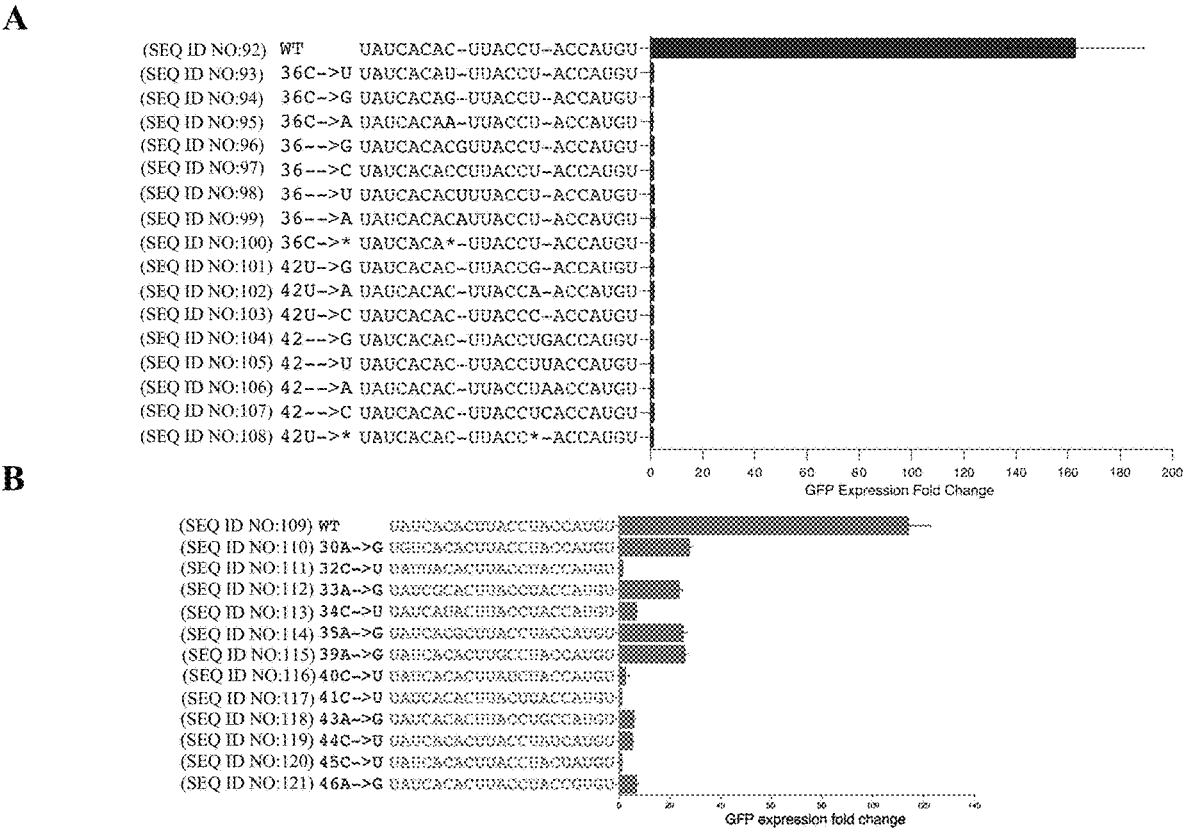
FIGS. 10A-10B demonstrate ultraspecific riboregulator detection based on the design in FIG. 1 of various single-nucleotide mutations. (A) In vivo verification of SNP discrimination for different mutation types at positions 36 and 42. (B) In vivo verification of the discrimination between wobble pairs and Watson-Crick pairs at different locations. Generally, the mutations where A is converted to G give higher gene expression compared to mutations where C is converted to U.

FIG. 9 demonstrates in vivo verification of SNP discrimination at each position along a SNP sensitive region. We observed significantly lower GFP expression in all the cells having mutant type RNA triggers as compared with cells having wide type RNA triggers. Cells having mutations at positions from 32 to 48 showed almost no GFP expression. In another in vivo assay (FIG. 10A), we verified specific discrimination for different mutation types (e.g., mutations, insertions, deletions) at position 36 and position 42. We also tested in vivo the ability of the ultraspecific riboregulators to distinguish between Watson-Crick base pairs and wobble base pairs (i.e. G-U pairing). Wobble base pairs incur only a slight energy penalty because they cause only partially reduce hydrogen bonding compared to canonical Watson-Crick base pairing. The ultraspecific riboregulator was tested by generating SNP target RNAs in which an A was converted to a G or a C was converted to U. FIG. 10B shows the results obtained from the test displaying significantly higher GFP expression for the perfect target compared to mutated targets with wobble pairing to the switch RNA. At least a 4-fold difference in gene expression was observed for all targets and, in general, the ultraspecific riboregulators proved better at discriminating C to U mutations rather than A to G.

Figure 11:
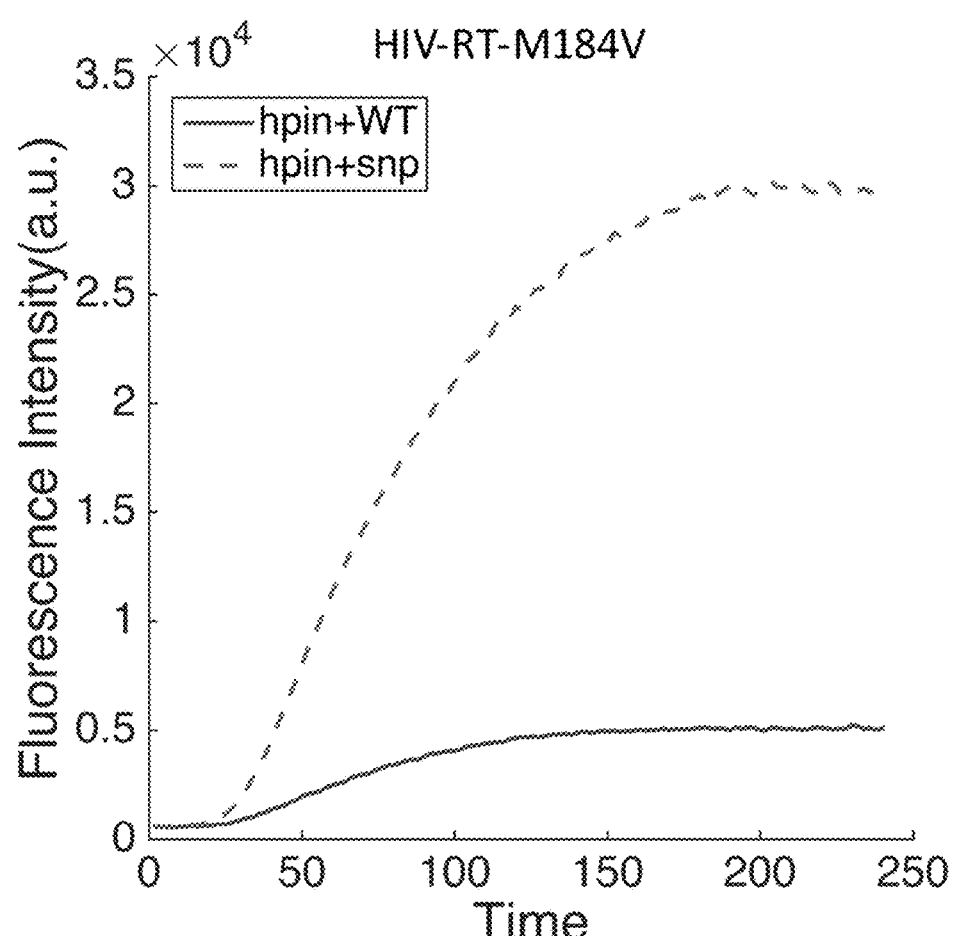
FIG. 11 demonstrates an ultraspecific riboregulator based on the design in FIG. 1 for detection of a drug-resistance conferring mutations in HIV. The ultra-specific riboregulator recognizes the mutation M184V in the HIV-1 reverse transcriptase conferring lamivudine resistance. SEQ ID NO:5 represents the riboregulator used. SEQ ID NO:6 represents the wild-type target sequence. SEQ ID NO:7 represents the SNP target sequence.

As shown in FIG. 11, ultraspecific riboregulators can be used to detect HIV mutations that confer drug resistance. The ultraspecific riboregulator recognized the mutation M184V in the HIV-1 reverse transcriptase, which confer resistance to lamivudine. The sequence of the sensor is as follows:

```
                                        (SEQ ID NO: 5)
GGGUCUAUGCUGCCCUAUUUCUAAGUCAACGUAAAUCGACAAAUCAUCC

ACGUAUUGAUACAAAUUAGAGGAGAUAGAACAUGUUGUAUCAAUACGUG

GAUGAUAAAACCGAUAAAACUAAAAGCAUGCGUAAAGGAGAAGAACUUU

UCACUGG
```

Figure 12:
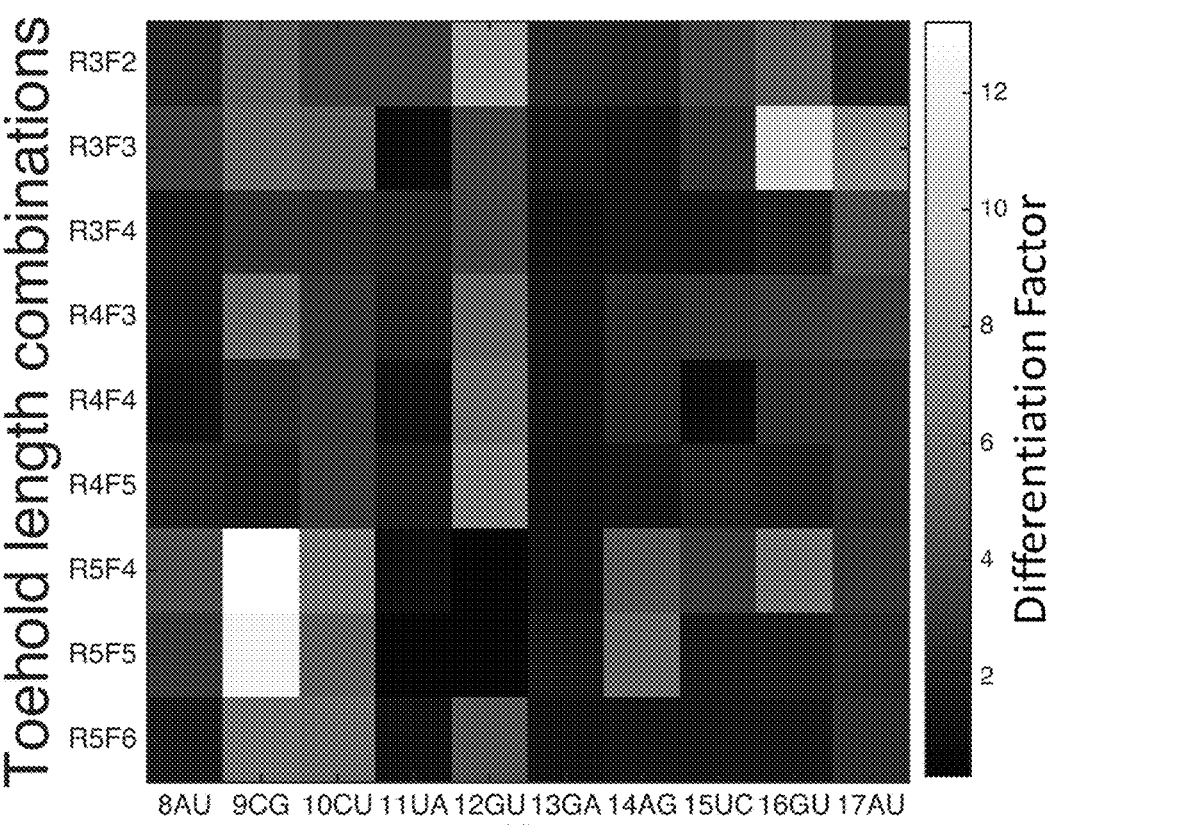
FIG. 12 is a heat map of the differentiation factor computed for ultraspecific riboregulators designed to recognize mutations of HIV-1 reverse transcriptase using different lengths of forward and reverse toehold domains. The riboregulators were engineered to differentiate the SNP from WT at any position. The heat map is shown in gray scale, in which the shading is increasing lighter as the differentiation factor increases.

The heat map in FIG. 12, which depicts the computed differentiation factor for various combinations of forward and reverse toehold lengths, demonstrates that ultraspecific riboregulators can be engineered to differentiate the SNP target from the WT target at any position. The discrimination performance can be maximized through the screening of different combinations of forward and reverse toehold lengths. The heat map is shown in gray scale, in which the shading is increasing lighter as the differentiation factor increases.

Figure 13:
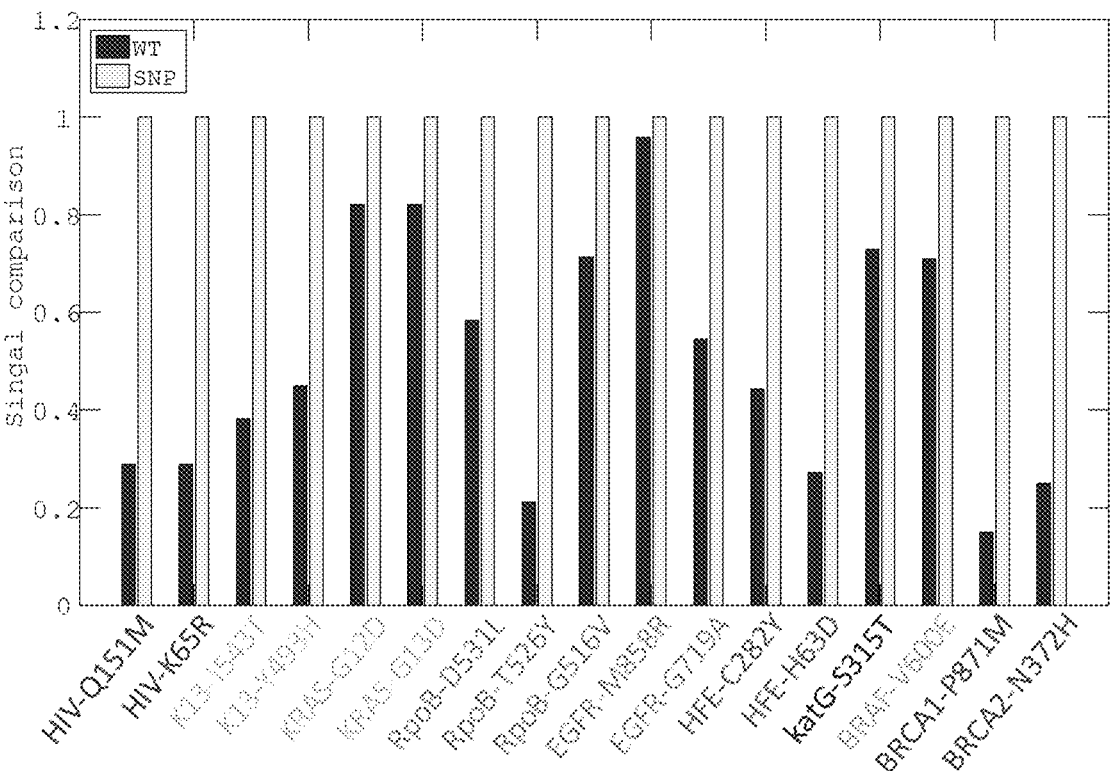
FIG. 13 illustrates signals detected for ultraspecific riboregulators based on the design in FIG. 1 capable of discriminating SNPs in vitro across 17 genes associated with a variety of different diseases and drug resistance-conferring mutations: HIV drug resistance (HIV-Q151, HIV-K65R); malaria resistance to artemisinin (K13-I543T, K13-Y493H); colorectal, breast, and other cancers (KRAS-G12D, KRAS-G13D, EGFR-M858R, EGFR-G719A, BRAF-V600E, BRCA1-P871M, BRCA2-N372H); rifampicin-resistant tuberculosis (RpoB-D531L, RpoB-T526Y, RpoB-G516V); isoniazid-resistant tuberculosis (katG-S315T); and the hereditary disease hemochromatosis (HFE-C282Y, HFE-H63D). The GFP signal measured for the perfectly complementary SNP target was normalized to 1 to facilitate comparison between different sensors challenged with the WT, non-disease-associated targets. SEQ ID NOs of the riboregulators used and the corresponding wild-type and SNP target sequences are listed below.

We also designed engineered riboregulators capable of discriminating SNPs across 10 genes associated with a variety of different diseases as well as drug resistance-conferring mutations (FIG. 13). Specifically, we designed ultraspecific riboregulators to detect the following target diseases/susceptibilities: HIV drug resistance (HIV-Q151, HIV-K65R); malaria resistance to artemisinin (K13-I543T, K13-Y493H); colorectal, breast, and other cancers (KRAS-G12D, KRAS-G13D, EGFR-M858R, EGFR-G719A, BRAF-V600E, BRCA1-P871M, BRCA2-N372H); rifampicin-resistant tuberculosis (RpoB-D531L, RpoB-T526Y, RpoB-G516V); isoniazid-resistant tuberculosis (katG-S315T); and the hereditary disease hemochromatosis (HFE-C282Y, HFE-H63D).

HIV-Q151M (SEQ ID NO: 8):
GGGUUUUGUCAUGCUACUUUGGAAUAUUCACUAACACACUUUCCAUCCC

AUUGGAAGCACUUCCCAACAGAGGAGACAGAAAAUGGGGAAGUGCUUCC

AAUGGGAUACCGAACCAAAUAAACUCCGAAUGCGUAAAGGAGAAGAACU

UUUCACUGG

HIV-K65R (SEQ ID NO: 11):
GGGAAGUUCUCUGAAAUCUACUAAUUUGGGAAGCGGAGUACUGUCUUUU

CUCUUUAUGGUACUGACUAGAGGAGACAGGCAAUGCAGUACCAUAAAGA

GAAAAGACAAAGAAACAAGAAAACAAGAAUGCGUAAAGGAGAAGAACUU

UUCACUGG

K13-I543T (SEQ ID NO: 14):
GGGAUAUGCUUCUACAUUCGGUAUAAUACUUCUUAAAAACAUAUCCCCA

GUACAAUAAAUAUCUCGACAGAGGAGAUAAACAAUGGAGAUAUUUAUUG

UACUGGGGAAUAAACAAAGACUAAACAAGAUGCGUAAAGGAGAAGAACU

UUUCACUGG

K13-Y493H (SEQ ID NO: 17):
GGGAGUUUCAAAUAAAGCCUUAUAAUCAGAACACACGGCACCAAAAACG

UGUAAGAAAUUACCAAACUAGAGGAGAUAAAACAUGUUGGUAAUUUCUU

ACACGUUUACUAACCCACUCACAACAUCCAUGCGUAAAGGAGAAGAACU

UUUCACUGG

KRAS-G12D (SEQ ID NO: 20):
GGGGAUUCUGAAUUAGCUGUAUCGGAUACUAAAGCUUGCCUACGCCAUC

AGCUCCAUUGCCAUCAGAGGAGAUAGAAAAUGGGCAAUGGAGCUGAUGG

CGUAAAUGAAAUAAGAAUGAACAAAAUGCGUAAAGGAGAAGAACUUUUC

ACUGG

KRAS-G13D (SEQ ID NO: 23):
GGGAAUGAUUCUGAAUUAGCUGUAGCUACCAUAAACUCUUGCCUACGUC

ACCAGCUUCCUUAACAGAGGAGAUGAAAAAUGAAGGAAGCUGGUGACGU

AGGCUCAAAUCAAAAACUAAGAAUAAUGCGUAAAGGAGAAGAACUUUUC

ACUGG

RpoB-D531L (SEQ ID NO: 26):
GGGACCGUCCGCAUCGAUCGGCGAAUUGGAAAGACAUACCACGUGGCGG

AGCUCCUCGUCCACGUAACAGAGGAGAUGAGAAAUGACGUGGACGAGGA

GCUCCGCCAAUAACAAAAUCAAACUAAAAUGCGUAAAGGAGAAGAACU

UUUCACUGG

RpoB-T526Y (SEQ ID NO: 29):
GGGCGGCGAAUUGGCCUGUGCCACCACGAACAUUAAAGCCUCGUCGGCG

UACAGGUACACCUCGUAACAGAGGAGAUAAGAAAUGACGAGGUGUACCU

GUACGCCGCAACUAAAACUAAACCCUCAAAUGCGUAAAGGAGAAGAACU

UUUCACUGG

RpoB-G516V (SEQ ID NO: 32):
GGGGUCCUCCUCGUCGGCGGUCAGGUACAACAAUAAUACGCUAACCACG

ACGUCGACCACGCCAAAACAGAGGAGACAACAUAUGUUGGCGUGGUCGA

CGUCGUGGCACUUAGCUCAGCCCCAAAUAAUGCGUAAAGGAGAAGAACU

UUUCACUGG

EGFR-M858R (SEQ ID NO: 35):
GGGCUUCUGCAUGGUAUUCUUUCUCUAAUAAGGUUUGCAGUUUGGCCCG

CCCAAAAUCCAGUUGGCAGAGGAGAUAAGGGAUGAACUGGAUUUUGGGC

GGGCCACGAACAAUACAACUACUAACCAUGCGUAAAGGAGAAGAACUUU

UCACUGG

EGFR-G719A (SEQ DI NO: 38):
GGGCUGGGAUCCAGAGUCCCUUAUACACAAAAUUUACACGCACCGGAGGC

CAGCACUUUCGCACACUAGAGGAGAUGAGGCAUGGUGCGAAAGUGCUGG

CCUCCGAAUAAACAAAGUGAAUCAAAAAUGCGUAAAGGAGAAGAACUUU

UCACUGG

HFE-C282Y (SEQ ID NO: 41):
GGGCCAGAUCACAAUGAGGGGCUGAUCCUAUAAACACGGCUCCACCUGG

UACGUAUAUCUCUCCAAACAGAGGAGAUAACACAUGUGGAGAGAUAUAC

GUACCAGGGAUAAGAAAAUAAGAAUAAAGAUGCGUAAAGGAGAAGAACU

UUUCACUGG

HFE-H63D (SEQ ID NO: 44):
GGGUCUACUGGAAACCCAUGGAGUUCGGGAUAUGUUAAGGCGACUCUCA

UCAUCAUAGAAGCGACAACAGAGGAGAUAAGAGAUGGUCGCUUCUAUGA

UGAUGAGAGGAGGCGGAAAACUAGAUAAAAUGCGUAAAGGAGAAGAACU

UUUCACUGG

KatG-S315T (SEQ ID NO: 47):
GGGGUUGUCCCAUUUCGUCGGGGUGUUCGUCAACUAAAAAGCGAUGCCG

GUGGUGAUCGCCCCGACGCGACAGAGGAGACAAAGCAUGGCGUCGGGGC

GAUCACCACCGAACAAAAUAACAACUUCUCAAAUGCGUAAAGGAGAAGA

ACUUUUCACUGG

BRAF-V600E (SEQ ID NO: 50):
GGGGUCCAGACAACUGUUCAAACUGAUGAAAUAGAAGACAUCGAGAUUUC

UCUGUAGCUAAUCGAACCAGAGGAGAUAGAGAAUGUCGAUUAGCUACAG

AGAAAUCGACAAAAGACAAGAUAAAAGAAUGCGUAAAGGAGAAGAACUU

UUCACUGG

BRCA1-P871L (SEQ ID NO: 53):
GGGAGAGAAUGUUGCACAUUCCUCUUCUACUAAACACAGAUUUGAAAAC

AGAGCAAAUGAAUUUGGCUAGAGGAGAUAAAAACAUGCAAAUUCAUUUGC

UCUGUUUUUCACAAUAAACAACUCCGAAAAAUGCGUAAAGGAGAAGAACU

UUUCACUGG.

BRCA2-N372H (SEQ ID NO: 56):
GGGAACUUCCUUGGAGAUUUUGUCACUGGAGUAAGAUAAGGGCUUCUGA

UGUGCUACAUAGGGCAACAGAGGAGAUAAAAGAUGGCCCUAUGUAGCAC

AUCAGAAACAAAUACAACUAAAAAUCAAAUGCGUAAAGGAGAAGAACUU

UUCACUGG.

Figures 14A, 14B, 14C, 14D:
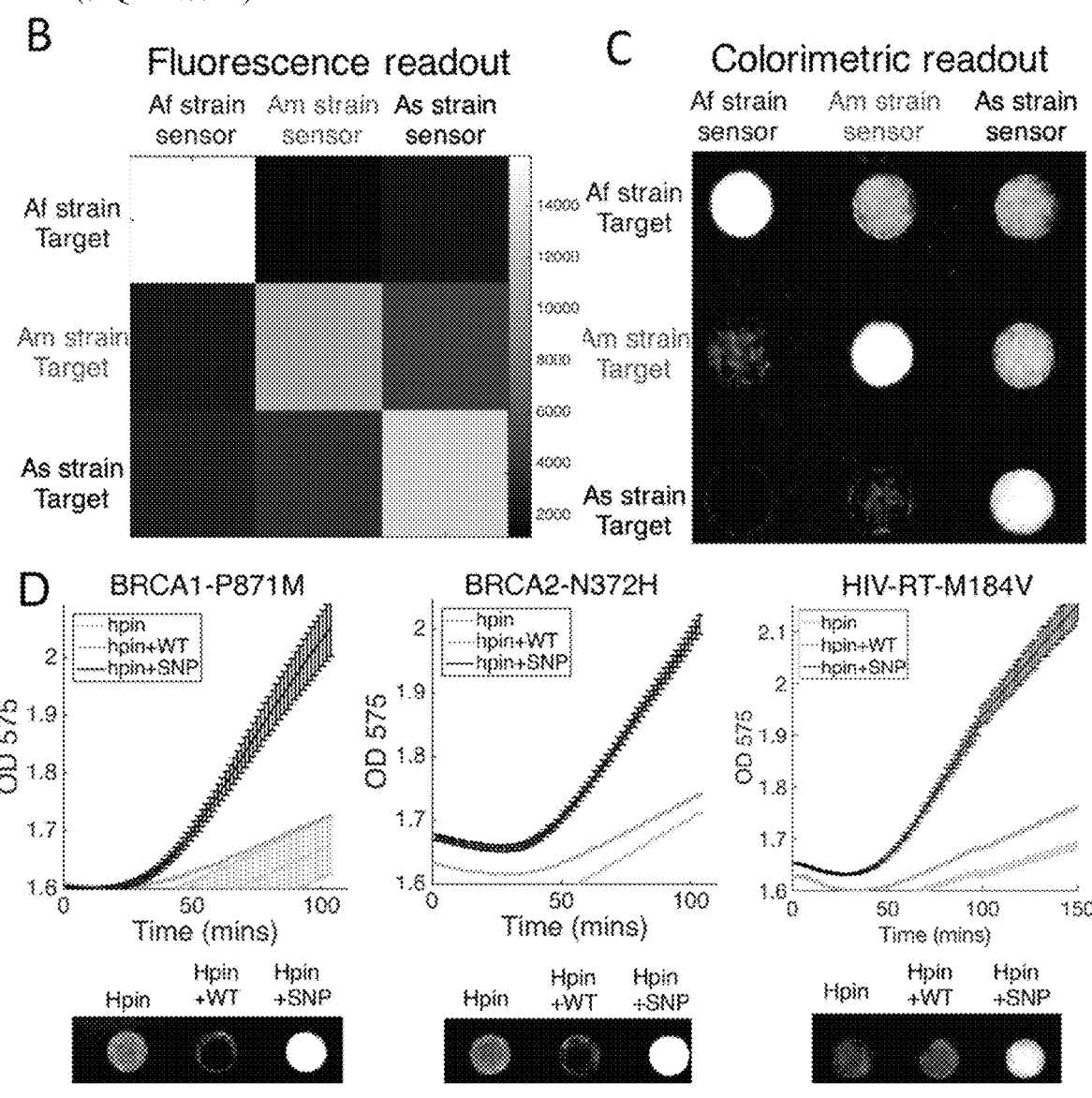

As shown in FIGS. 14A-14D, we verified paper-based mutation detection using ultraspecific riboregulators for a variety of different closely related sequences. FIGS. 14A-14C demonstrate the use of ultraspecific riboregulators for identification of three different strains of the Zika virus circulating in Africa, the Americas, and Asia. These strains are very closely related, yet only the strain from the Americas has been connected to the incidence of birth defects. FIG. 14A shows the sequence differences between the target RNAs detected by the riboregulators. FIG. 14B displays results of testing the riboregulators using GFP as the output protein demonstrating significantly increased protein expression when the strain sensing riboregulator is exposed to its corresponding Zika virus strain. FIG. 14C provides a photograph of a paper-based detection reaction in which the riboregulators express the enzyme lacZ. Clear color differences are observed for the riboregulators with their cognate virus strains. The paper-based colorimetric reactions can also successfully discriminate between target RNAs differing by only a single nucleotide. FIG. 14D shows detection of three different SNP targets in three genes: BRCA1-P871L, BRCA2-N372H, and HIV-RT-M184V. For mutant targets, the riboregulator was in the "OPEN" ("ON") state, and expression of beta-galactosidase turned the substrate to a different color. The photographs in FIGS. 14C-14D have been adjusted so that the color changes that are clearly visible in color images can be seen in grayscale reproductions.

In Vitro Validation of Ultraspecific Riboregulators Lacking Docking Sites

FIGS. 15A-15B illustrate the principle for engineered ultraspecific riboregulators lacking a docking region and a spacer region. In these riboregulators, the transition between the OPEN ("ON") and CLOSE ("OFF") states is a bimolecular reaction and the use of a very short forward toehold without the docking site means that device operation is much more effective in in vitro settings. The relationship between the differentiation factor and reaction energy of the wild-type (non-cognate) target and the riboregulator hairpin is plotted in FIG. 15B. FIG. 16 demonstrates experimental verification in cell-free reactions of the bimolecular mechanism to discriminate SNP targets with wild-type targets, where the encoded protein is green fluorescence protein (GFP). FIGS. 17A-17B display systematic in vitro studies of ultraspecific riboregulator performance against a series of different mutated targets. The ultraspecific riboregulator without the docking and spacer sites can correctly identify the perfect target while discriminating mutant targets with modifications throughout its entire length, along with insertions and deletions.

We claim:

1. An ultraspecific riboregulator comprising a bimolecular RNA complex comprising (a) a first RNA comprising, in a 5' to 3' direction, a ribosomal binding site, start codon, sensor binding region, and a coding domain encoding a reporter protein; and (b) a second RNA comprising a sequence that is bound to the first RNA at the sensor binding region, wherein the second RNA has partial or full complementarity with a target RNA molecule, and a toehold sequence that is not bound to the first RNA, and wherein the toehold sequence has partial or full complementarity to the target RNA molecule.

2. The ultraspecific riboregulator of claim 1, wherein the toehold sequence is located at the 3' end of the second RNA.

3. The ultraspecific riboregulator of claim 1, wherein the toehold sequence is located at the 5' end of the second RNA.

4. A method for detecting a target RNA molecule in a sample, the method comprising:

contacting the ultraspecific riboregulator of claim 1 to the sample, wherein, if present in the sample, the target RNA molecule will bind to the toehold sequence and displace the second RNA sequence that is partially bound to the sensor binding region of the first RNA; and detecting expression of the reporter protein, wherein reporter protein expression indicates the presence of the target RNA in the sample.

5. The method of claim 4, wherein the target RNA molecule is selected from the group consisting of a messenger RNA (mRNA) molecule, microRNA, small interfering RNA (siRNA), antisense RNA, non-coding RNA, mRNA splice variant, an RNA with chemically modified bases, and an RNA with non-canonical bases.

6. The method of claim 4, wherein the sample is a biological sample.

7. The method of claim 4, wherein detecting the target RNA molecule indicates the presence of a microorganism, pathogen, mutation, or gene in the sample.

8. The method of claim 7, wherein the gene comprises one or more mutations relative to another gene.

9. The method of claim 4, wherein detecting the target RNA molecule indicates the absence of a microorganism, pathogen, mutation or gene in the sample.

10. The method of claim 9, wherein the gene comprises one or more mutations relative to another gene.

11. A method for detecting a target RNA molecule in a sample, the method comprising:

contacting an ultraspecific riboregulator to the sample, wherein the riboregulator is a synthetic nucleic acid molecule comprising a fully or partially double-stranded stem domain; a loop domain; a ribosomal binding site; a start codon; a toehold sequence between the stem domain and a spacer domain; a docking domain; wherein the spacer domain is between the toehold sequence and the docking domain; and a coding sequence encoding a reporter protein; wherein the toehold sequence and the docking domain are complementary to the target RNA molecule; wherein the spacer domain is not complementary to the target RNA molecule; wherein the spacer domain creates a bulge between the riboregulator and the target RNA molecule; and wherein, if present in the sample, the target RNA molecule will bind to and displace one strand of the double-stranded stem domain; and detecting expression of the reporter protein, wherein reporter protein expression indicates the presence of the target RNA in the sample.

12. The method of claim 11, wherein the target RNA molecule is selected from the group consisting of a messenger RNA (mRNA) molecule, microRNA, small interfering RNA (siRNA), antisense RNA, non-coding RNA, mRNA splice variant, an RNA with chemically modified bases, and an RNA with non-canonical bases.

13. The method of claim 11, wherein the sample is a biological sample.

14. The method of claim 11, wherein detecting the target RNA molecule indicates the presence of a microorganism, pathogen, mutation, or gene in the sample.

15. The method of claim 11, wherein detecting the target RNA molecule indicates the absence of a microorganism, pathogen, mutation, or gene in the sample.

16. A method for detecting a target RNA molecule in a sample, the method comprising:

contacting an ultraspecific riboregulator to the sample, wherein the riboregulator is a synthetic nucleic acid molecule comprising a fully or partially double-stranded stem domain; a loop domain comprising a ribosomal binding site and a start codon; a toehold sequence; and a coding sequence encoding a reporter protein; wherein the stem domain and the toehold sequence are complementary to the target RNA molecule; and wherein, if present in the sample, the target RNA molecule will bind to and displace one strand of the double-stranded stem domain; and detecting expression of the reporter protein, wherein reporter protein expression indicates the presence of the target RNA in the sample.

17. The method of claim 16, wherein the target RNA molecule is selected from the group consisting of a messenger RNA (mRNA) molecule, microRNA, small interfering RNA (siRNA), antisense RNA, non-coding RNA, mRNA splice variant, an RNA with chemically modified bases, and an RNA with non-canonical bases.

18. The method of claim 16, wherein the sample is a biological sample.

19. The method of claim 16, wherein detecting the target RNA molecule indicates the presence of a microorganism, pathogen, mutation, or gene in the sample.

20. The method of claim 16, wherein detecting the target RNA molecule indicates the absence of a microorganism, pathogen, mutation, or gene in the sample.

* * * * *

```
                         SEQUENCE LISTING

Sequence total quantity: 127
SEQ ID NO: 1            moltype = RNA  length = 130
FEATURE                 Location/Qualifiers
misc_feature            1..130
                        note = synthetic
source                  1..130
                        mol_type = other RNA
                        organism = synthetic construct
SEQUENCE: 1
gggcattatt taccatatca tatccaagat tacatttaca acagaggaga taacgaatgg  60
taaatgtaat cttggatatg aaacaactaa cactaatccg catgcgtaaa ggagaagaac  120
ttttcactgg                                                         130

SEQ ID NO: 2            moltype = RNA  length = 110
FEATURE                 Location/Qualifiers
source                  1..110
                        mol_type = other RNA
                        organism = Plasmodium falciparum
SEQUENCE: 2
tttttccaaa tgtattaaaa tagatggaaa tcccgtttca tacgcttgta aatgtaatct  60
tggatatgat atggtaaata atgtttgtat accaaatgaa tgtaagaatg              110

SEQ ID NO: 3            moltype = RNA  length = 130
FEATURE                 Location/Qualifiers
misc_feature            1..130
                        note = synthetic
source                  1..130
                        mol_type = other RNA
                        organism = synthetic construct
SEQUENCE: 3
gggtttcgct ctattctcat cagtttcatg tcctgtgtca ctagaggaga taacgaatgg  60
acacaggaca tgaaactgat gtaccaacta aactacccct catgcgtaaa ggagaagaac  120
ttttcactgg                                                         130

SEQ ID NO: 4            moltype = RNA  length = 150
FEATURE                 Location/Qualifiers
source                  1..150
                        mol_type = other RNA
                        organism = Zika virus
SEQUENCE: 4
gggccagcac agtgggatga tcgttaatga cacaggacat gaaactgatg agaatagagc  60
gaaagttgag ataacgccca attccaag agccgaagcc accctggggg ggtttggaag  120
cctaggactt gattgtgaac cgaggacagg                                   150

SEQ ID NO: 5            moltype = RNA  length = 154
FEATURE                 Location/Qualifiers
misc_feature            1..154
                        note = synthetic
```

-continued

```
source                    1..154
                          mol_type = other RNA
                          organism = synthetic construct
SEQUENCE: 5
gggtctatgc tgccctattt ctaagtcaac gtaaatcgac aaatcatcca cgtattgata    60
caaattagag gagatagaac atgttgtatc aatacgtgga tgataaaacc gataaaacta   120
aaagcatgcg taaaggagaa gaacttttca ctgg                                154

SEQ ID NO: 6              moltype = DNA  length = 57
FEATURE                   Location/Qualifiers
source                    1..57
                          mol_type = other DNA
                          organism = Human immunodeficiency virus 1
SEQUENCE: 6
tatcaataca tggatgattt gtatgtagga tctgacttag aaatagggca gcataga        57

SEQ ID NO: 7              moltype = DNA  length = 57
FEATURE                   Location/Qualifiers
misc_feature              1..57
                          note = synthetic
source                    1..57
                          mol_type = other DNA
                          organism = synthetic construct
SEQUENCE: 7
tatcaatacg tggatgattt gtatgtagga tctgacttag aaatagggca gcataga        57

SEQ ID NO: 8              moltype = RNA  length = 156
FEATURE                   Location/Qualifiers
misc_feature              1..156
                          note = synthetic
source                    1..156
                          mol_type = other RNA
                          organism = synthetic construct
SEQUENCE: 8
gggttttgtc atgctacttt ggaatattca ctaacacact ttccatccca ttggaagcac    60
ttcccaacag aggagacaga aaatggggaa gtgcttccaa tgggataccg aaccaaataa   120
actccgaatg cgtaaaggag aagaactttt cactgg                              156

SEQ ID NO: 9              moltype = DNA  length = 57
FEATURE                   Location/Qualifiers
source                    1..57
                          mol_type = other DNA
                          organism = Human immunodeficiency virus 1
SEQUENCE: 9
gtgcttccac agggatggaa aggatcacca gcaatattcc aaagtagcat gacaaaa        57

SEQ ID NO: 10             moltype = DNA  length = 57
FEATURE                   Location/Qualifiers
misc_feature              1..57
                          note = synthetic
source                    1..57
                          mol_type = other DNA
                          organism = synthetic construct
SEQUENCE: 10
gtgcttccaa tgggatggaa aggatcacca gcaatattcc aaagtagcat gacaaaa        57

SEQ ID NO: 11             moltype = RNA  length = 155
FEATURE                   Location/Qualifiers
misc_feature              1..155
                          note = synthetic
source                    1..155
                          mol_type = other RNA
                          organism = synthetic construct
SEQUENCE: 11
gggaagttct ctgaaatcta ctaatttggg aagcggagta ctgtcttttc tctttatggt    60
actgactaga ggagacaggc aatgcagtac cataaagaga aaagacaaag aaacaagaaa   120
acaagaatgc gtaaaggaga agaacttttc actgg                               155

SEQ ID NO: 12             moltype = DNA  length = 57
FEATURE                   Location/Qualifiers
source                    1..57
                          mol_type = other DNA
                          organism = Human immunodeficiency virus 1
SEQUENCE: 12
gccataaaga aaaaagacag tactaaatgg agaaaattag tagatttcag agaactt        57

SEQ ID NO: 13             moltype = DNA  length = 57
FEATURE                   Location/Qualifiers
misc_feature              1..57
```

-continued

```
                        note = synthetic
source                  1..57
                        mol_type = other DNA
                        organism = synthetic construct
SEQUENCE: 13
gccataaaga gaaaagacag tactaaatgg agaaaattag tagatttcag agaactt      57

SEQ ID NO: 14           moltype = RNA   length = 156
FEATURE                 Location/Qualifiers
misc_feature            1..156
                        note = synthetic
source                  1..156
                        mol_type = other RNA
                        organism = synthetic construct
SEQUENCE: 14
gggatatgct tctacattcg gtataatact tcttaaaaca tatcccccag tacaataaat   60
atctcgacag aggagataaa caatggagat atttattgta ctggggaata aacaaagact   120
aaacaagatg cgtaaaggag aagaactttt cactgg                             156

SEQ ID NO: 15           moltype = DNA   length = 57
FEATURE                 Location/Qualifiers
source                  1..57
                        mol_type = other DNA
                        organism = Plasmodium falciparum
SEQUENCE: 15
atttattgta ttgggggata tgatggctct tctattatac cgaatgtaga agcatat      57

SEQ ID NO: 16           moltype = DNA   length = 57
FEATURE                 Location/Qualifiers
misc_feature            1..57
                        note = synthetic
source                  1..57
                        mol_type = other DNA
                        organism = synthetic construct
SEQUENCE: 16
atttattgta ctgggggata tgatggctct tctattatac cgaatgtaga agcatat      57

SEQ ID NO: 17           moltype = RNA   length = 156
FEATURE                 Location/Qualifiers
misc_feature            1..156
                        note = synthetic
source                  1..156
                        mol_type = other RNA
                        organism = synthetic construct
SEQUENCE: 17
gggagtttca aataaagcct tataatcaga acacacggca ccaaaaacgt gtaagaaatt   60
accaaactag aggagataaa acatgttggt aatttcttac acgtttacta acccactcac   120
aacatccatg cgtaaaggag aagaactttt cactgg                             156

SEQ ID NO: 18           moltype = DNA   length = 57
FEATURE                 Location/Qualifiers
source                  1..57
                        mol_type = other DNA
                        organism = Plasmodium falciparum
SEQUENCE: 18
aatttcttat acgttttggg tggtaataac tatgattata aggctttatt tgaaact      57

SEQ ID NO: 19           moltype = DNA   length = 57
FEATURE                 Location/Qualifiers
misc_feature            1..57
                        note = synthetic
source                  1..57
                        mol_type = other DNA
                        organism = synthetic construct
SEQUENCE: 19
aatttcttac acgttttggg tggtaataac tatgattata aggctttatt tgaaact      57

SEQ ID NO: 20           moltype = RNA   length = 152
FEATURE                 Location/Qualifiers
misc_feature            1..152
                        note = synthetic
source                  1..152
                        mol_type = other RNA
                        organism = synthetic construct
SEQUENCE: 20
ggggattctg aattagctgt atcggatact aaagcttgcc tacgccatca gctccattgc   60
catcagagga gatagaaaat gggcaatgga gctgatggcg taaatgaaat aagaatgaac   120
aaaatgcgta aaggagaaga acttttcact gg                                 152
```

```
SEQ ID NO: 21               moltype = RNA   length = 57
FEATURE                     Location/Qualifiers
source                      1..57
                            mol_type = other RNA
                            organism = Homo sapiens
SEQUENCE: 21
gttggagctg gtggcgtagg caagagtgcc ttgacgatac agctaattca gaatcat        57

SEQ ID NO: 22               moltype = RNA   length = 57
FEATURE                     Location/Qualifiers
misc_feature                1..57
                            note = synthetic
source                      1..57
                            mol_type = other RNA
                            organism = synthetic construct
SEQUENCE: 22
gttggagctg atggcgtagg caagagtgcc ttgacgatac agctaattca gaatcat        57

SEQ ID NO: 23               moltype = RNA   length = 152
FEATURE                     Location/Qualifiers
misc_feature                1..152
                            note = synthetic
source                      1..152
                            mol_type = other RNA
                            organism = synthetic construct
SEQUENCE: 23
gggaatgatt ctgaattagc tgtagctacc ataaactctt gcctacgtca ccagcttcct     60
taacagagga gatgaaaaat gaaggaagct ggtgacgtag gctcaaatca aaaactaaga    120
ataatgcgta aaggagaaga acttttcact gg                                  152

SEQ ID NO: 24               moltype = RNA   length = 57
FEATURE                     Location/Qualifiers
source                      1..57
                            mol_type = other RNA
                            organism = Homo sapiens
SEQUENCE: 24
ggagctggtg gcgtaggcaa gagtgccttg acgatacagc taattcagaa tcatttt        57

SEQ ID NO: 25               moltype = RNA   length = 57
FEATURE                     Location/Qualifiers
misc_feature                1..57
                            note = synthetic
source                      1..57
                            mol_type = other RNA
                            organism = synthetic construct
SEQUENCE: 25
ggagctggtg acgtaggcaa gagtgccttg acgatacagc taattcagaa tcatttt        57

SEQ ID NO: 26               moltype = RNA   length = 156
FEATURE                     Location/Qualifiers
misc_feature                1..156
                            note = synthetic
source                      1..156
                            mol_type = other RNA
                            organism = synthetic construct
SEQUENCE: 26
gggaccgtcc gcatcgatcg gcgaattgga aagacatacc acgtggcgga gctcctcgtc     60
cacgtaacag aggagatgag aaatgacgtg gacgaggagc tccgccaata acaaaatcaa    120
aactaaaatg cgtaaaggag aagaactttt cactgg                             156

SEQ ID NO: 27               moltype = DNA   length = 57
FEATURE                     Location/Qualifiers
source                      1..57
                            mol_type = other DNA
                            organism = Mycobacterium tuberculosis
SEQUENCE: 27
gacgaggagg accgccacgt ggtggcacag gccaattcgc cgatcgatgc ggacggt        57

SEQ ID NO: 28               moltype = DNA   length = 57
FEATURE                     Location/Qualifiers
misc_feature                1..57
                            note = synthetic
source                      1..57
                            mol_type = other DNA
                            organism = synthetic construct
SEQUENCE: 28
gacgaggagc tccgccacgt ggtggcacag gccaattcgc cgatcgatgc ggacggt        57

SEQ ID NO: 29               moltype = RNA   length = 156
```

-continued

```
FEATURE            Location/Qualifiers
misc_feature       1..156
                   note = synthetic
source             1..156
                   mol_type = other RNA
                   organism = synthetic construct
SEQUENCE: 29
gggcggcgaa ttggcctgtg ccaccacgaa cattaaagcc tcgtcggcgt acaggtacac    60
ctcgtaacag aggagataag aaatgacgag gtgtacctgt acgccgcaac taaaactaaa   120
ccctcaaatg cgtaaaggag aagaactttt cactgg                             156

SEQ ID NO: 30      moltype = DNA   length = 57
FEATURE            Location/Qualifiers
source             1..57
                   mol_type = other DNA
                   organism = Mycobacterium tuberculosis
SEQUENCE: 30
gtgtacctga ccgccgacga ggaggaccgc cacgtggtgg cacaggccaa ttcgccg       57

SEQ ID NO: 31      moltype = DNA   length = 57
FEATURE            Location/Qualifiers
misc_feature       1..57
                   note = synthetic
source             1..57
                   mol_type = other DNA
                   organism = synthetic construct
SEQUENCE: 31
gtgtacctgt acgccgacga ggaggaccgc cacgtggtgg cacaggccaa ttcgccg       57

SEQ ID NO: 32      moltype = RNA   length = 156
FEATURE            Location/Qualifiers
misc_feature       1..156
                   note = synthetic
source             1..156
                   mol_type = other RNA
                   organism = synthetic construct
SEQUENCE: 32
ggggtcctcc tcgtcggcgg tcaggtacaa caataatacg ctaaccacga cgtcgaccac    60
gccaaaacag aggagacaac atatgttggc gtggtcgacg tcgtggcact tagctcagcc   120
ccaaataatg cgtaaaggag aagaactttt cactgg                             156

SEQ ID NO: 33      moltype = DNA   length = 57
FEATURE            Location/Qualifiers
source             1..57
                   mol_type = other DNA
                   organism = Mycobacterium tuberculosis
SEQUENCE: 33
gtggtcgacg gcgtggttag cgacgagatc gtgtacctga ccgccgacga ggaggac       57

SEQ ID NO: 34      moltype = DNA   length = 57
FEATURE            Location/Qualifiers
misc_feature       1..57
                   note = synthetic
source             1..57
                   mol_type = other DNA
                   organism = synthetic construct
SEQUENCE: 34
gtggtcgacg tcgtggttag cgacgagatc gtgtacctga ccgccgacga ggaggac       57

SEQ ID NO: 35      moltype = RNA   length = 154
FEATURE            Location/Qualifiers
misc_feature       1..154
                   note = synthetic
source             1..154
                   mol_type = other RNA
                   organism = synthetic construct
SEQUENCE: 35
gggcttctgc atggtattct ttctctaata aggtttgcag tttggcccgc ccaaaatcca    60
gttggcagag gagataaggg atgaactgga ttttgggcgg gccacgaaca atacaactac   120
taaccatgcg taaaggagaa gaacttttca ctgg                               154

SEQ ID NO: 36      moltype = RNA   length = 57
FEATURE            Location/Qualifiers
source             1..57
                   mol_type = other RNA
                   organism = Homo sapiens
SEQUENCE: 36
gattttgggc tggccaaact gctgggtgcg gaagagaaag aataccatgc agaagga       57
```

-continued

```
SEQ ID NO: 37          moltype = RNA   length = 57
FEATURE                Location/Qualifiers
misc_feature           1..57
                       note = synthetic
source                 1..57
                       mol_type = other RNA
                       organism = synthetic construct
SEQUENCE: 37
gattttgggc gggccaaact gctgggtgcg gaagagaaag aataccatgc agaagga        57

SEQ ID NO: 38          moltype = RNA   length = 154
FEATURE                Location/Qualifiers
misc_feature           1..154
                       note = synthetic
source                 1..154
                       mol_type = other RNA
                       organism = synthetic construct
SEQUENCE: 38
gggctgggat ccagagtccc ttatacacaa atttacacgc accggaggcc agcactttcg      60
cacactagag gagatgaggc atggtgcgaa agtgctggcc tccgaataaa caaagtgaat     120
caaaaatgcg taaaggagaa gaacttttca ctgg                                 154

SEQ ID NO: 39          moltype = RNA   length = 57
FEATURE                Location/Qualifiers
source                 1..57
                       mol_type = other RNA
                       organism = Homo sapiens
SEQUENCE: 39
aaagtgctgg gctccggtgc gttcggcacg gtgtataagg gactctggat cccagaa        57

SEQ ID NO: 40          moltype = RNA   length = 57
FEATURE                Location/Qualifiers
misc_feature           1..57
                       note = synthetic
source                 1..57
                       mol_type = other RNA
                       organism = synthetic construct
SEQUENCE: 40
aaagtgctgg cctccggtgc gttcggcacg gtgtataagg gactctggat cccagaa        57

SEQ ID NO: 41          moltype = RNA   length = 156
FEATURE                Location/Qualifiers
misc_feature           1..156
                       note = synthetic
source                 1..156
                       mol_type = other RNA
                       organism = synthetic construct
SEQUENCE: 41
gggccagatc acaatgaggg gctgatccta taaacacggc tccacctggt acgtatatct      60
ctccaaacag aggagataac acatgtggag agatatacgt accagggata agaaaataag     120
aataaagatg cgtaaaggag aagaactttt cactgg                              156

SEQ ID NO: 42          moltype = RNA   length = 60
FEATURE                Location/Qualifiers
source                 1..60
                       mol_type = other RNA
                       organism = Homo sapiens
SEQUENCE: 42
gggagatata cgtgccaggt ggagcaccca ggcctggatc agccctcat tgtgatctgg       60

SEQ ID NO: 43          moltype = RNA   length = 60
FEATURE                Location/Qualifiers
misc_feature           1..60
                       note = synthetic
source                 1..60
                       mol_type = other RNA
                       organism = synthetic construct
SEQUENCE: 43
gggagatata cgtaccaggt ggagcaccca ggcctggatc agccctcat tgtgatctgg       60

SEQ ID NO: 44          moltype = RNA   length = 156
FEATURE                Location/Qualifiers
misc_feature           1..156
                       note = synthetic
source                 1..156
                       mol_type = other RNA
                       organism = synthetic construct
SEQUENCE: 44
gggtctactg gaaacccatg gagttcggga tatgttaagg cgactctcat catcatagaa      60
```

```
gcgacaacag aggagataag agatggtcgc ttctatgatg atgagaggag gcggaaaact   120
agataaaatg cgtaaaggag aagaactttt cactgg                             156

SEQ ID NO: 45          moltype = RNA   length = 60
FEATURE                Location/Qualifiers
source                 1..60
                       mol_type = other RNA
                       organism = Homo sapiens
SEQUENCE: 45
gggttctatg atcatgagag tcgccgtgtg gagccccgaa ctccatgggt ttccagtaga   60

SEQ ID NO: 46          moltype = RNA   length = 60
FEATURE                Location/Qualifiers
misc_feature           1..60
                       note = synthetic
source                 1..60
                       mol_type = other RNA
                       organism = synthetic construct
SEQUENCE: 46
gggttctatg atgatgagag tcgccgtgtg gagccccgaa ctccatgggt ttccagtaga   60

SEQ ID NO: 47          moltype = RNA   length = 159
FEATURE                Location/Qualifiers
misc_feature           1..159
                       note = synthetic
source                 1..159
                       mol_type = other RNA
                       organism = synthetic construct
SEQUENCE: 47
ggggttgtcc catttcgtcg gggtgttcgt caactaaaaa gcgatgccgg tggtgatcgc   60
cccgacgcga cagaggagac aaagcatggc gtcggggcga tcaccaccga acaaaataac   120
aacttctcaa atgcgtaaag gagaagaact tttcactgg                          159

SEQ ID NO: 48          moltype = RNA   length = 60
FEATURE                Location/Qualifiers
source                 1..60
                       mol_type = other RNA
                       organism = Mycobacterium tuberculosis
SEQUENCE: 48
ggggcgatca ccagcggcat cgaggtcgta tggacgaaca ccccgacgaa atgggacaac   60

SEQ ID NO: 49          moltype = RNA   length = 60
FEATURE                Location/Qualifiers
misc_feature           1..60
                       note = synthetic
source                 1..60
                       mol_type = other RNA
                       organism = synthetic construct
SEQUENCE: 49
ggggcgatca ccaccggcat cgaggtcgta tggacgaaca ccccgacgaa atgggacaac   60

SEQ ID NO: 50          moltype = RNA   length = 155
FEATURE                Location/Qualifiers
misc_feature           1..155
                       note = synthetic
source                 1..155
                       mol_type = other RNA
                       organism = synthetic construct
SEQUENCE: 50
gggtccagac aactgttcaa actgatgaaa tagaagacat cgagatttct ctgtagctaa   60
tcgaaccaga ggagatagag aatgtcgatt agctacagag aaatcgacaa aagacaagat   120
aaaagaatgc gtaaaggaga agaacttttc actgg                             155

SEQ ID NO: 51          moltype = RNA   length = 57
FEATURE                Location/Qualifiers
source                 1..57
                       mol_type = other RNA
                       organism = Homo sapiens
SEQUENCE: 51
ctagctacag tgaaatctcg atggagtggg tcccatcagt ttgaacagtt gtctgga       57

SEQ ID NO: 52          moltype = RNA   length = 57
FEATURE                Location/Qualifiers
misc_feature           1..57
                       note = synthetic
source                 1..57
                       mol_type = other RNA
                       organism = synthetic construct
SEQUENCE: 52
```

-continued

```
ctagctacag agaaatctcg atggagtggg tcccatcagt ttgaacagtt gtctgga        57

SEQ ID NO: 53              moltype = RNA   length = 156
FEATURE                    Location/Qualifiers
misc_feature               1..156
                           note = synthetic
source                     1..156
                           mol_type = other RNA
                           organism = synthetic construct
SEQUENCE: 53
gggagagaat gttgcacatt cctcttctac taaacacaga tttgaaaaca gagcaaatga        60
atttggctag aggagataaa acatgcaaat tcatttgctc tgttttcaca ataaacaact       120
ccgaaaaatg cgtaaaggag aagaactttt cactgg                                 156

SEQ ID NO: 54              moltype = RNA   length = 60
FEATURE                    Location/Qualifiers
source                     1..60
                           mol_type = other RNA
                           organism = Homo sapiens
SEQUENCE: 54
gggtcatttg ctccgttttc aaatccagga aatgcagaag aggaatgtgc aacattctct        60

SEQ ID NO: 55              moltype = RNA   length = 60
FEATURE                    Location/Qualifiers
misc_feature               1..60
                           note = synthetic
source                     1..60
                           mol_type = other RNA
                           organism = synthetic construct
SEQUENCE: 55
gggtcatttg ctctgttttc aaatccagga aatgcagaag aggaatgtgc aacattctct        60

SEQ ID NO: 56              moltype = RNA   length = 155
FEATURE                    Location/Qualifiers
misc_feature               1..155
                           note = synthetic
source                     1..155
                           mol_type = other RNA
                           organism = synthetic construct
SEQUENCE: 56
gggaacttcc ttggagattt tgtcactgga gtaagataag ggcttctgat gtgctacata        60
gggcaacaga ggagataaaa gatggcccta tgtagcacat cagaaacaaa tacaactaaa       120
aatcaaatgc gtaaaggaga agaacttttc actgg                                  155

SEQ ID NO: 57              moltype = RNA   length = 60
FEATURE                    Location/Qualifiers
source                     1..60
                           mol_type = other RNA
                           organism = Homo sapiens
SEQUENCE: 57
gggaatgtag caaatcagaa gccctttgag agtggaagtg acaaaatctc caaggaagtt        60

SEQ ID NO: 58              moltype = RNA   length = 60
FEATURE                    Location/Qualifiers
misc_feature               1..60
                           note = synthetic
source                     1..60
                           mol_type = other RNA
                           organism = synthetic construct
SEQUENCE: 58
gggaatgtag cacatcagaa gccctttgag agtggaagtg acaaaatctc caaggaagtt        60

SEQ ID NO: 59              moltype = RNA   length = 154
FEATURE                    Location/Qualifiers
misc_feature               1..154
                           note = synthetic
source                     1..154
                           mol_type = other RNA
                           organism = synthetic construct
SEQUENCE: 59
gggtatgacc cgctttccag cctttgtaac ctttccggcg atttcatttc cgtttctcag        60
actactagag gagataaaac atgagtctga gaaacggaaa tgaaacaaga ctaaataaca       120
acataatgcg taaaggagaa gaacttttca ctgg                                   154

SEQ ID NO: 60              moltype = RNA   length = 57
FEATURE                    Location/Qualifiers
source                     1..57
                           mol_type = other RNA
                           organism = Zika virus
```

-continued

```
                                strain = African Zika virus
SEQUENCE: 60
gtgagaaacg gaaatgaaat cgcagcctgt ctgacaaagg ctggaaagcg ggtcata      57

SEQ ID NO: 61              moltype = RNA   length = 154
FEATURE                    Location/Qualifiers
misc_feature               1..154
                           note = synthetic
source                     1..154
                           mol_type = other RNA
                           organism = synthetic construct
SEQUENCE: 61
gggtatgacc cgtttccag cctttgtcag tcccccatag atctcattgc cgttcctcag      60
actaacagag gagataaaag atgagtctga ggaacggcaa tgagtacacc aataaaaccc     120
taaaaatgcg taaaggagaa gaacttttca ctgg                                 154

SEQ ID NO: 62              moltype = RNA   length = 57
FEATURE                    Location/Qualifiers
source                     1..57
                           mol_type = other RNA
                           organism = Zika virus
                           strain = American Zika Virus
SEQUENCE: 62
gtgaggaacg gcaatgagat cgcagcttgt ctgacaaagg ctggaaaacg ggtcata       57

SEQ ID NO: 63              moltype = RNA   length = 154
FEATURE                    Location/Qualifiers
misc_feature               1..154
                           note = synthetic
source                     1..154
                           mol_type = other RNA
                           organism = synthetic construct
SEQUENCE: 63
gggtatgacc cgtttccag cctttgtcta cctaataccg atctcattgc cattcctcag      60
actattagag gagataagac atgagtctga ggaatggcaa tgagaaaact aaaaaactaa     120
aaatgatgcg taaaggagaa gaacttttca ctgg                                 154

SEQ ID NO: 64              moltype = RNA   length = 57
FEATURE                    Location/Qualifiers
source                     1..57
                           mol_type = other RNA
                           organism = Zika virus
                           strain = Asian Zika virus
SEQUENCE: 64
gtgaggaatg gcaatgagat cgcagcttgt ctgacaaagg ctggaaaacg ggtcata       57

SEQ ID NO: 65              moltype = RNA   length = 154
FEATURE                    Location/Qualifiers
misc_feature               1..154
                           note = synthetic
source                     1..154
                           mol_type = other RNA
                           organism = synthetic construct
SEQUENCE: 65
gggtatgacc cgctttccag cctttgtctc cctttacgcg atttcatttc cgtttctcag     60
actgaaagag gagatgggaa atgagtctga gaaacggaaa tgaaaaaaaa actaaaacta    120
aaaaaatgac catgattacg gattcactgg ccgt                                 154

SEQ ID NO: 66              moltype = RNA   length = 154
FEATURE                    Location/Qualifiers
misc_feature               1..154
                           note = synthetic
source                     1..154
                           mol_type = other RNA
                           organism = synthetic construct
SEQUENCE: 66
gggtatgacc cgtttccag cctttgtcag tcccataaag atctcattgc cgttcctcag      60
actataagag gagagtaaaa atgagtctga ggaacggcaa tgagcaaaaa aagataaaaa     120
aacaaatgac catgattacg gattcactgg ccgt                                 154

SEQ ID NO: 67              moltype = RNA   length = 154
FEATURE                    Location/Qualifiers
misc_feature               1..154
                           note = synthetic
source                     1..154
                           mol_type = other RNA
                           organism = synthetic construct
SEQUENCE: 67
gggtatgacc cgtttccag cctttgtcta aattataacg atctcattgc cattcctcag      60
```

-continued

```
actgaaagag gagatgaaga atgagtctga ggaatggcaa tgagaaaaaa aacagaacta  120
aaaatatgac catgattacg gattcactgg ccgt                             154

SEQ ID NO: 68           moltype = RNA   length = 155
FEATURE                 Location/Qualifiers
misc_feature            1..155
                        note = synthetic
source                  1..155
                        mol_type = other RNA
                        organism = synthetic construct
SEQUENCE: 68
gggagagaat gttgcacatt cctcttctga actaacaaaa tttgaaaaca gagcaaatga   60
atttgctaga ggagataaaa catgaaattc atttgctctg ttttccacaa taaacaactc  120
cgaaaaatgc gtaaaggaga agaacttttc actgg                            155

SEQ ID NO: 69           moltype = RNA   length = 155
FEATURE                 Location/Qualifiers
misc_feature            1..155
                        note = synthetic
source                  1..155
                        mol_type = other RNA
                        organism = synthetic construct
SEQUENCE: 69
gggaacttcc ttggagattt tgtcacttat ggaaaattag ggcttctgat gtgctacata   60
gggcaacaga ggagataaaa gatggcccta tgtagcacat cagaaacaaa tacaactaaa  120
aatcaaatgc gtaaaggaga agaacttttc actgg                            155

SEQ ID NO: 70           moltype = RNA   length = 21
FEATURE                 Location/Qualifiers
misc_feature            1..21
                        note = synthetic
source                  1..21
                        mol_type = other RNA
                        organism = synthetic construct
SEQUENCE: 70
tatcacactt acctaccatg t                                            21

SEQ ID NO: 71           moltype = RNA   length = 21
FEATURE                 Location/Qualifiers
misc_feature            1..21
                        note = synthetic
source                  1..21
                        mol_type = other RNA
                        organism = synthetic construct
SEQUENCE: 71
catcacactt acctaccatg t                                            21

SEQ ID NO: 72           moltype = RNA   length = 21
FEATURE                 Location/Qualifiers
misc_feature            1..21
                        note = synthetic
source                  1..21
                        mol_type = other RNA
                        organism = synthetic construct
SEQUENCE: 72
tctcacactt acctaccatg t                                            21

SEQ ID NO: 73           moltype = RNA   length = 21
FEATURE                 Location/Qualifiers
misc_feature            1..21
                        note = synthetic
source                  1..21
                        mol_type = other RNA
                        organism = synthetic construct
SEQUENCE: 73
taccacactt acctaccatg t                                            21

SEQ ID NO: 74           moltype = RNA   length = 21
FEATURE                 Location/Qualifiers
misc_feature            1..21
                        note = synthetic
source                  1..21
                        mol_type = other RNA
                        organism = synthetic construct
SEQUENCE: 74
tataacactt acctaccatg t                                            21

SEQ ID NO: 75           moltype = RNA   length = 21
FEATURE                 Location/Qualifiers
```

-continued

```
misc_feature              1..21
                          note = synthetic
source                    1..21
                          mol_type = other RNA
                          organism = synthetic construct
SEQUENCE: 75
tatcccactt acctaccatg t                                                    21

SEQ ID NO: 76             moltype = RNA   length = 21
FEATURE                   Location/Qualifiers
misc_feature              1..21
                          note = synthetic
source                    1..21
                          mol_type = other RNA
                          organism = synthetic construct
SEQUENCE: 76
tatcaaactt acctaccatg t                                                    21

SEQ ID NO: 77             moltype = RNA   length = 21
FEATURE                   Location/Qualifiers
misc_feature              1..21
                          note = synthetic
source                    1..21
                          mol_type = other RNA
                          organism = synthetic construct
SEQUENCE: 77
tatcaccctt acctaccatg t                                                    21

SEQ ID NO: 78             moltype = RNA   length = 21
FEATURE                   Location/Qualifiers
misc_feature              1..21
                          note = synthetic
source                    1..21
                          mol_type = other RNA
                          organism = synthetic construct
SEQUENCE: 78
tatcacattt acctaccatg t                                                    21

SEQ ID NO: 79             moltype = RNA   length = 21
FEATURE                   Location/Qualifiers
misc_feature              1..21
                          note = synthetic
source                    1..21
                          mol_type = other RNA
                          organism = synthetic construct
SEQUENCE: 79
tatcacacct acctaccatg t                                                    21

SEQ ID NO: 80             moltype = RNA   length = 21
FEATURE                   Location/Qualifiers
misc_feature              1..21
                          note = synthetic
source                    1..21
                          mol_type = other RNA
                          organism = synthetic construct
SEQUENCE: 80
tatcacactc acctaccatg t                                                    21

SEQ ID NO: 81             moltype = RNA   length = 21
FEATURE                   Location/Qualifiers
misc_feature              1..21
                          note = synthetic
source                    1..21
                          mol_type = other RNA
                          organism = synthetic construct
SEQUENCE: 81
tatcacactt ccctaccatg t                                                    21

SEQ ID NO: 82             moltype = RNA   length = 21
FEATURE                   Location/Qualifiers
misc_feature              1..21
                          note = synthetic
source                    1..21
                          mol_type = other RNA
                          organism = synthetic construct
SEQUENCE: 82
tatcacactt aactaccatg t                                                    21

SEQ ID NO: 83             moltype = RNA   length = 21
```

-continued

```
FEATURE            Location/Qualifiers
misc_feature       1..21
                   note = synthetic
source             1..21
                   mol_type = other RNA
                   organism = synthetic construct
SEQUENCE: 83
tatcacactt acataccatg t                                                    21

SEQ ID NO: 84      moltype = RNA   length = 21
FEATURE            Location/Qualifiers
misc_feature       1..21
                   note = synthetic
source             1..21
                   mol_type = other RNA
                   organism = synthetic construct
SEQUENCE: 84
tatcacactt acccaccatg t                                                    21

SEQ ID NO: 85      moltype = RNA   length = 21
FEATURE            Location/Qualifiers
misc_feature       1..21
                   note = synthetic
source             1..21
                   mol_type = other RNA
                   organism = synthetic construct
SEQUENCE: 85
tatcacactt acctcccatg t                                                    21

SEQ ID NO: 86      moltype = RNA   length = 21
FEATURE            Location/Qualifiers
misc_feature       1..21
                   note = synthetic
source             1..21
                   mol_type = other RNA
                   organism = synthetic construct
SEQUENCE: 86
tatcacactt acctaacatg t                                                    21

SEQ ID NO: 87      moltype = RNA   length = 21
FEATURE            Location/Qualifiers
misc_feature       1..21
                   note = synthetic
source             1..21
                   mol_type = other RNA
                   organism = synthetic construct
SEQUENCE: 87
tatcacactt acctacaatg t                                                    21

SEQ ID NO: 88      moltype = RNA   length = 21
FEATURE            Location/Qualifiers
misc_feature       1..21
                   note = synthetic
source             1..21
                   mol_type = other RNA
                   organism = synthetic construct
SEQUENCE: 88
tatcacactt acctaccctg t                                                    21

SEQ ID NO: 89      moltype = RNA   length = 21
FEATURE            Location/Qualifiers
misc_feature       1..21
                   note = synthetic
source             1..21
                   mol_type = other RNA
                   organism = synthetic construct
SEQUENCE: 89
tatcacactt acctaccagg t                                                    21

SEQ ID NO: 90      moltype = RNA   length = 21
FEATURE            Location/Qualifiers
misc_feature       1..21
                   note = synthetic
source             1..21
                   mol_type = other RNA
                   organism = synthetic construct
SEQUENCE: 90
tatcacactt acctaccatc t                                                    21
```

```
SEQ ID NO: 91          moltype = RNA   length = 21
FEATURE                Location/Qualifiers
misc_feature           1..21
                       note = synthetic
source                 1..21
                       mol_type = other RNA
                       organism = synthetic construct
SEQUENCE: 91
tatcacactt acctaccatg c                                                    21

SEQ ID NO: 92          moltype = RNA   length = 21
FEATURE                Location/Qualifiers
misc_feature           1..21
                       note = synthetic
source                 1..21
                       mol_type = other RNA
                       organism = synthetic construct
SEQUENCE: 92
tatcacactt acctaccatg t                                                    21

SEQ ID NO: 93          moltype = RNA   length = 21
FEATURE                Location/Qualifiers
misc_feature           1..21
                       note = synthetic
source                 1..21
                       mol_type = other RNA
                       organism = synthetic construct
SEQUENCE: 93
tatcacattt acctaccatg t                                                    21

SEQ ID NO: 94          moltype = RNA   length = 21
FEATURE                Location/Qualifiers
misc_feature           1..21
                       note = synthetic
source                 1..21
                       mol_type = other RNA
                       organism = synthetic construct
SEQUENCE: 94
tatcacagtt acctaccatg t                                                    21

SEQ ID NO: 95          moltype = RNA   length = 21
FEATURE                Location/Qualifiers
misc_feature           1..21
                       note = synthetic
source                 1..21
                       mol_type = other RNA
                       organism = synthetic construct
SEQUENCE: 95
tatcacaatt acctaccatg t                                                    21

SEQ ID NO: 96          moltype = RNA   length = 22
FEATURE                Location/Qualifiers
misc_feature           1..22
                       note = synthetic
source                 1..22
                       mol_type = other RNA
                       organism = synthetic construct
SEQUENCE: 96
tatcacacgt tacctaccat gt                                                   22

SEQ ID NO: 97          moltype = RNA   length = 22
FEATURE                Location/Qualifiers
misc_feature           1..22
                       note = synthetic
source                 1..22
                       mol_type = other RNA
                       organism = synthetic construct
SEQUENCE: 97
tatcacacct tacctaccat gt                                                   22

SEQ ID NO: 98          moltype = RNA   length = 22
FEATURE                Location/Qualifiers
misc_feature           1..22
                       note = synthetic
source                 1..22
                       mol_type = other RNA
                       organism = synthetic construct
SEQUENCE: 98
tatcacactt tacctaccat gt                                                   22
```

```
SEQ ID NO: 99            moltype = RNA   length = 22
FEATURE                  Location/Qualifiers
misc_feature             1..22
                         note = synthetic
source                   1..22
                         mol_type = other RNA
                         organism = synthetic construct
SEQUENCE: 99
tatcacacat tacctaccat gt                                                    22

SEQ ID NO: 100           moltype = RNA   length = 20
FEATURE                  Location/Qualifiers
misc_feature             1..20
                         note = synthetic
source                   1..20
                         mol_type = other RNA
                         organism = synthetic construct
SEQUENCE: 100
tatcacatta cctaccatgt                                                       20

SEQ ID NO: 101           moltype = RNA   length = 21
FEATURE                  Location/Qualifiers
misc_feature             1..21
                         note = synthetic
source                   1..21
                         mol_type = other RNA
                         organism = synthetic construct
SEQUENCE: 101
tatcacactt accgaccatg t                                                     21

SEQ ID NO: 102           moltype = RNA   length = 21
FEATURE                  Location/Qualifiers
misc_feature             1..21
                         note = synthetic
source                   1..21
                         mol_type = other RNA
                         organism = synthetic construct
SEQUENCE: 102
tatcacactt accaaccatg t                                                     21

SEQ ID NO: 103           moltype = RNA   length = 21
FEATURE                  Location/Qualifiers
misc_feature             1..21
                         note = synthetic
source                   1..21
                         mol_type = other RNA
                         organism = synthetic construct
SEQUENCE: 103
tatcacactt acccaccatg t                                                     21

SEQ ID NO: 104           moltype = RNA   length = 22
FEATURE                  Location/Qualifiers
misc_feature             1..22
                         note = synthetic
source                   1..22
                         mol_type = other RNA
                         organism = synthetic construct
SEQUENCE: 104
tatcacactt acctgaccat gt                                                    22

SEQ ID NO: 105           moltype = RNA   length = 22
FEATURE                  Location/Qualifiers
misc_feature             1..22
                         note = synthetic
source                   1..22
                         mol_type = other RNA
                         organism = synthetic construct
SEQUENCE: 105
tatcacactt accttaccat gt                                                    22

SEQ ID NO: 106           moltype = RNA   length = 22
FEATURE                  Location/Qualifiers
misc_feature             1..22
                         note = synthetic
source                   1..22
                         mol_type = other RNA
                         organism = synthetic construct
SEQUENCE: 106
```

-continued

```
tatcacactt acctaaccat gt                                              22

SEQ ID NO: 107          moltype = RNA   length = 22
FEATURE                 Location/Qualifiers
misc_feature            1..22
                        note = synthetic
source                  1..22
                        mol_type = other RNA
                        organism = synthetic construct
SEQUENCE: 107
tatcacactt acctcaccat gt                                              22

SEQ ID NO: 108          moltype = RNA   length = 20
FEATURE                 Location/Qualifiers
misc_feature            1..20
                        note = synthetic
source                  1..20
                        mol_type = other RNA
                        organism = synthetic construct
SEQUENCE: 108
tatcacactt accaccatgt                                                 20

SEQ ID NO: 109          moltype = RNA   length = 21
FEATURE                 Location/Qualifiers
misc_feature            1..21
                        note = synthetic
source                  1..21
                        mol_type = other RNA
                        organism = synthetic construct
SEQUENCE: 109
tatcacactt acctaccatg t                                               21

SEQ ID NO: 110          moltype = RNA   length = 21
FEATURE                 Location/Qualifiers
misc_feature            1..21
                        note = synthetic
source                  1..21
                        mol_type = other RNA
                        organism = synthetic construct
SEQUENCE: 110
tgtcacactt acctaccatg t                                               21

SEQ ID NO: 111          moltype = RNA   length = 21
FEATURE                 Location/Qualifiers
misc_feature            1..21
                        note = synthetic
source                  1..21
                        mol_type = other RNA
                        organism = synthetic construct
SEQUENCE: 111
tattacactt acctaccatg t                                               21

SEQ ID NO: 112          moltype = RNA   length = 21
FEATURE                 Location/Qualifiers
misc_feature            1..21
                        note = synthetic
source                  1..21
                        mol_type = other RNA
                        organism = synthetic construct
SEQUENCE: 112
tatcgcactt acctaccatg t                                               21

SEQ ID NO: 113          moltype = RNA   length = 21
FEATURE                 Location/Qualifiers
misc_feature            1..21
                        note = synthetic
source                  1..21
                        mol_type = other RNA
                        organism = synthetic construct
SEQUENCE: 113
tatcatactt acctaccatg t                                               21

SEQ ID NO: 114          moltype = RNA   length = 21
FEATURE                 Location/Qualifiers
misc_feature            1..21
                        note = synthetic
source                  1..21
                        mol_type = other RNA
                        organism = synthetic construct
```

```
SEQUENCE: 114
tatcacgctt acctaccatg t                                              21

SEQ ID NO: 115          moltype = RNA   length = 21
FEATURE                 Location/Qualifiers
misc_feature            1..21
                        note = synthetic
source                  1..21
                        mol_type = other RNA
                        organism = synthetic construct
SEQUENCE: 115
tatcacactt gcctaccatg t                                              21

SEQ ID NO: 116          moltype = RNA   length = 21
FEATURE                 Location/Qualifiers
misc_feature            1..21
                        note = synthetic
source                  1..21
                        mol_type = other RNA
                        organism = synthetic construct
SEQUENCE: 116
tatcacactt atctaccatg t                                              21

SEQ ID NO: 117          moltype = RNA   length = 21
FEATURE                 Location/Qualifiers
misc_feature            1..21
                        note = synthetic
source                  1..21
                        mol_type = other RNA
                        organism = synthetic construct
SEQUENCE: 117
tatcacactt acttaccatg t                                              21

SEQ ID NO: 118          moltype = RNA   length = 21
FEATURE                 Location/Qualifiers
misc_feature            1..21
                        note = synthetic
source                  1..21
                        mol_type = other RNA
                        organism = synthetic construct
SEQUENCE: 118
tatcacactt acctgccatg t                                              21

SEQ ID NO: 119          moltype = RNA   length = 21
FEATURE                 Location/Qualifiers
misc_feature            1..21
                        note = synthetic
source                  1..21
                        mol_type = other RNA
                        organism = synthetic construct
SEQUENCE: 119
tatcacactt acctatcatg t                                              21

SEQ ID NO: 120          moltype = RNA   length = 21
FEATURE                 Location/Qualifiers
misc_feature            1..21
                        note = synthetic
source                  1..21
                        mol_type = other RNA
                        organism = synthetic construct
SEQUENCE: 120
tatcacactt acctactatg t                                              21

SEQ ID NO: 121          moltype = RNA   length = 21
FEATURE                 Location/Qualifiers
misc_feature            1..21
                        note = synthetic
source                  1..21
                        mol_type = other RNA
                        organism = synthetic construct
SEQUENCE: 121
tatcacactt acctaccgtg t                                              21

SEQ ID NO: 122          moltype = RNA   length = 19
FEATURE                 Location/Qualifiers
source                  1..19
                        mol_type = other RNA
                        organism = Human immunodeficiency virus 1
SEQUENCE: 122
```

```
tatcaataca tggatgatt                                                    19

SEQ ID NO: 123          moltype = RNA   length = 19
FEATURE                 Location/Qualifiers
misc_feature            1..19
                        note = synthetic
source                  1..19
                        mol_type = other RNA
                        organism = synthetic construct
SEQUENCE: 123
tatcaatata tggatgatt                                                    19

SEQ ID NO: 124          moltype = RNA   length = 28
FEATURE                 Location/Qualifiers
source                  1..28
                        mol_type = other RNA
                        organism = Human immunodeficiency virus 1
SEQUENCE: 124
tatcaataca tggatgattt gtatgtag                                          28

SEQ ID NO: 125          moltype = RNA   length = 34
FEATURE                 Location/Qualifiers
source                  1..34
                        mol_type = other RNA
                        organism = Zika virus
                        strain = American Zika Virus
SEQUENCE: 125
gtgaggaacg gcaatgagat cgcagcttgt ctga                                   34

SEQ ID NO: 126          moltype = RNA   length = 34
FEATURE                 Location/Qualifiers
source                  1..34
                        mol_type = other RNA
                        organism = Zika virus
                        strain = African Zika virus
SEQUENCE: 126
gtgaggaatg gcaatgagat cgcagcttgt ctga                                   34

SEQ ID NO: 127          moltype = RNA   length = 34
FEATURE                 Location/Qualifiers
source                  1..34
                        mol_type = other RNA
                        organism = Zika virus
                        strain = African Zika virus
SEQUENCE: 127
gtgagaaacg gaaatgaaat cgcagcctgt ctga                                   34
```